United States Patent
McShane et al.

(10) Patent No.: US 6,906,042 B2
(45) Date of Patent: Jun. 14, 2005

(54) MICELLES

(75) Inventors: James McShane, Wake Forest, NC (US); Tori Arens, Raleigh, NC (US); Kazuhiro Kaneko, Tsukuba (JP); Tomohiro Watanabe, Tsukuba (JP); Kazuhide Ashizawa, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/204,227

(22) PCT Filed: Feb. 20, 2001

(86) PCT No.: PCT/US01/05297
§ 371 (c)(1),
(2), (4) Date: Oct. 3, 2002

(87) PCT Pub. No.: WO01/60382
PCT Pub. Date: Aug. 23, 2001

(65) Prior Publication Data
US 2003/0216331 A1 Nov. 20, 2003

Related U.S. Application Data

(60) Provisional application No. 60/183,768, filed on Feb. 18, 2000.

(51) Int. Cl.[7] .................... A61K 31/70; C07H 5/00
(52) U.S. Cl. .................. 514/53; 536/17.1; 536/17.2; 536/18.7; 536/55; 536/55.2; 536/55.3; 424/400

(58) Field of Search ............... 424/400; 514/53; 536/17.1, 17.2, 18.7, 55, 55.2, 55.3

(56) References Cited

U.S. PATENT DOCUMENTS

| | | | |
|---|---|---|---|
| 5,681,824 A | 10/1997 | Christ et al. | |
| 5,750,664 A | 5/1998 | Christ et al. | |

*Primary Examiner*—Elli Peselev
(74) *Attorney, Agent, or Firm*—Wilmer Cutler Pickering Hale and Dorr LLP

(57) ABSTRACT

The invention provides micelles, pharmaceutical formulations comprising micells, solutions comprising micells, methods for preparing micells, methods for delivering micells to patients, and methods for treating sepsis, endotoxemia, septic shock and systemic inflamatory response syndrome in patients by adiministering micelles. The micelles comprises compounds of Forumala (A):

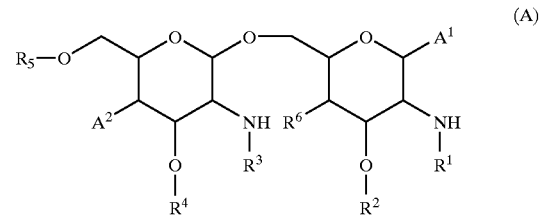

(A)

wherein the substituents are as defined herein.

96 Claims, 3 Drawing Sheets

MICELLES

RELATED APPLICATION

This application is a 371 of PCT/US01/05297 filed Feb. 20, 2001, which claims priority to U.S. Provisional Application No. 60/183,768 filed Feb. 18, 2000.

FIELD OF THE INVENTION

The present invention provides micelles, solutions comprising micelles, methods for preparing micelles, and methods for delivering micelles to patients. The micelles have fixed, preselected hydrodynamic diameters and are formed from basic or acidic amphiphilic compounds.

BACKGROUND OF THE INVENTION

Amphiphilic compounds are compounds with hydrophilic (water-loving) and hydrophobic (water-fearing) regions. When dispersed in water at a concentration above their critical micelle concentration or "CMC," amphiphilic compounds spontaneously self-associate into micelles. Micelles have a size which depends on properties of the solvent in which they are dispersed. The size of micelles can vary from approximately two to several hundreds of nanometers in equivalent spherical diameter.

When a drug is an amphiphilic compound which forms micelles when formulated for intravenous administration, the pharmacokinetics of the drug can depend upon the size of the micelle formed. Pharmacokinetics describes the time course of the distribution of a drug within the body after administration. The pharmacokinetics of a drug can affect its efficacy, metabolism, distribution, and/or toxicity in the body, either positively or negatively. For other routes of administration, micelle size can also influence pharmacokinetics. When the drug is in the form of a micelle, the effectiveness of delivery of the drug to the site of action depends upon the size of the aggregate, as the micelle size might affect diffusion, transport across cell membranes, and interactions with enzymes, transport proteins and lipids.

Prior to the work of the present inventors, the micelle size of amphiphilic drug compounds in water was known to be governed by the state of the solution, so once the formulation of the drug was chosen, a predetermined micelle size distribution was expected to result. The ability to control the micelle size of a drug delivered in a pharmaceutical formulation was severely limited, and control of the rate of delivery of drug to the site of action, therefore, was limited due to the inability to control the size of the micelle in solutions.

There is a need in the art to control or fix the size of micelles formed by amphiphilic drug compounds in aqueous solutions so that drug delivery rates and pharmacokinetics can be controlled. The present invention is directed to these, as well as other, important ends.

SUMMARY OF THE INVENTION

The present invention provides methods for preparing micelles comprising providing an amount of least one acidic amphiphilic compound, wherein the acidic amphiphilic compound comprises at least one ionizable group; adding the acidic amphiphilic compound to a first aqueous alkaline solution; wherein the first aqueous alkaline solution comprises at least one basic metal salt and at least one neutral metal salt; wherein the first aqueous alkaline solution has a predetermined metal ion concentration; wherein the concentration of acidic amphiphilic compound in the first aqueous solution is higher than the critical micelle concentration of the acidic amphiphilic compound; and wherein the pH and the metal ion concentration of the first aqueous alkaline solution are effective to form micelles with a preselected hydrodynamic diameter; thereby forming a second aqueous solution comprising micelles of the acidic amphiphilic compound with a preselected hydrodynamic diameter. The methods may further comprise adding the second aqueous alkaline solution to a third aqueous solution, wherein the third aqueous solution comprises a buffer system or at least one strong acid; thereby forming a fourth aqueous solution having a neutral pH relative to the pH of the second aqueous alkaline solution, wherein the micelles in the fourth aqueous solution have a fixed, preselected hydrodynamic diameter that is substantially the same as the fixed, preselected hydrodynamic diameter of the micelles in the second aqueous alkaline solution.

The present invention also provides methods for preparing micelles comprising providing an amount of least one basic amphiphilic compound that comprises at least one ionizable group; adding the basic amphiphilic compound to a first aqueous acidic solution; wherein the first aqueous solution comprises at least one protic acidic and at least one neutral metal salt; wherein the first aqueous solution has a predetermined metal ion concentration; wherein the concentration of basic amphiphilic compound in the first aqueous solution is higher than the critical micelle concentration of the basic amphiphilic compound; wherein the acidic pH and the metal ion concentration of the first aqueous solution are effective to form micelles with a preselected hydrodynamic diameter; thereby forming a second aqueous solution comprising micelles of the acidic amphiphilic compound with a preselected hydrodynamic diameter. The methods may further comprise adding the second aqueous solution to a third aqueous solution, wherein the third aqueous solution comprises a buffer system or at least one strong base; thereby forming a fourth aqueous solution having a neutral pH relative to the pH of the second aqueous acidic solution, wherein the micelles in the fourth aqueous solution have a fixed, preselected hydrodynamic diameter that is substantially the same as the fixed, preselected hydrodynamic diameter of the micelles in the second aqueous acidic solution.

The present invention also provides novel micelles, novel aqueous solutions comprising micelles, and novel methods of delivering micelles and/or aqueous solutions comprising micelles to patients.

These and other aspects of the present invention are described in detail below.

DETAILED DESCRIPTION OF THE INVENTION

Amphiphilic compounds, as used herein, refer to compounds with hydrophilic and hydrophobic moieties, which form micelles when dispersed in aqueous solutions. The amphiphilic compounds of the invention preferably comprise at least one ionizable group.

Critical micelle concentration ("CMC"), as used herein, is the concentration of amphiphilic compound at which micelles begin to spontaneously form in an aqueous solution. A "low" critical micelle concentration is preferably less than $10^{-6}$ g/ml.

Micelle, as used herein, refers to any water soluble aggregate which is spontaneously and reversibly formed from amphiphilic compounds or ions.

Hydrodynamic diameter of a micelle indicates that the micelle has the same hydrodynamic properties (e.g., diffusion coefficient) as a sphere of the same diameter. For example, a micelle having a width of 5 nm and a length of 9 nm might have a hydrodynamic diameter of 7 nm.

The present inventors have discovered a method for preparing micelles with fixed (i.e., stable), preseselected hydrodynamic diameters where the hydrodynamic diameter of micelles formed at an acidic or basic pH remains substantially the same at the acidic or basic pH; and the hydrodynamic diameter of the micelles remains substantially the same after adjustment of the acidic or basic pH to a second more neutral pH value (i.e., a neutral relative to the acidic or basic pH), where it would normally be expected that the hydrodynamic diameter of the micelles would increase. This discovery provides methods to produce pharmaceutical formulations of micelles with fixed, preselected hydrodynamic diameters. Using the methods of the invention, micelles having optimal hydrodynamic diameters can be used to design drug formulations that yield optimally desired pharmacokinetic and drug delivery properties.

The methods described herein are applicable to all acidic or basic amphiphilic compounds for which the critical micelle concentration is low. Preferably the acidic or basic amphiphilic compounds comprise at least one ionizable group. For formulations where the critical concentration is low, the salt concentration of the drug formulation must be kept sufficiently low to provide the required stability of the hydrodynamic diameter of the micelles. Thus; the stability of the hydrodynamic diameter of the micelles formed from such a process is governed by the critical micelle concentration and the pair inter-particle potential energy.

The micelles can grow in hydrodynamic diameter via a monomer mediated process similar to crystal ripening. The rate of hydrodynamic diameter increase is proportional to the monomer concentration (i.e., critical micelle concentration). For systems with a low critical micelle concentration, the rate of micelle hydrodynamic diameter increase via this mechanism can be sufficiently slow to allow the micelles to be stable for the amount of time required to be useful as pharmaceutical products.

Figure 1:
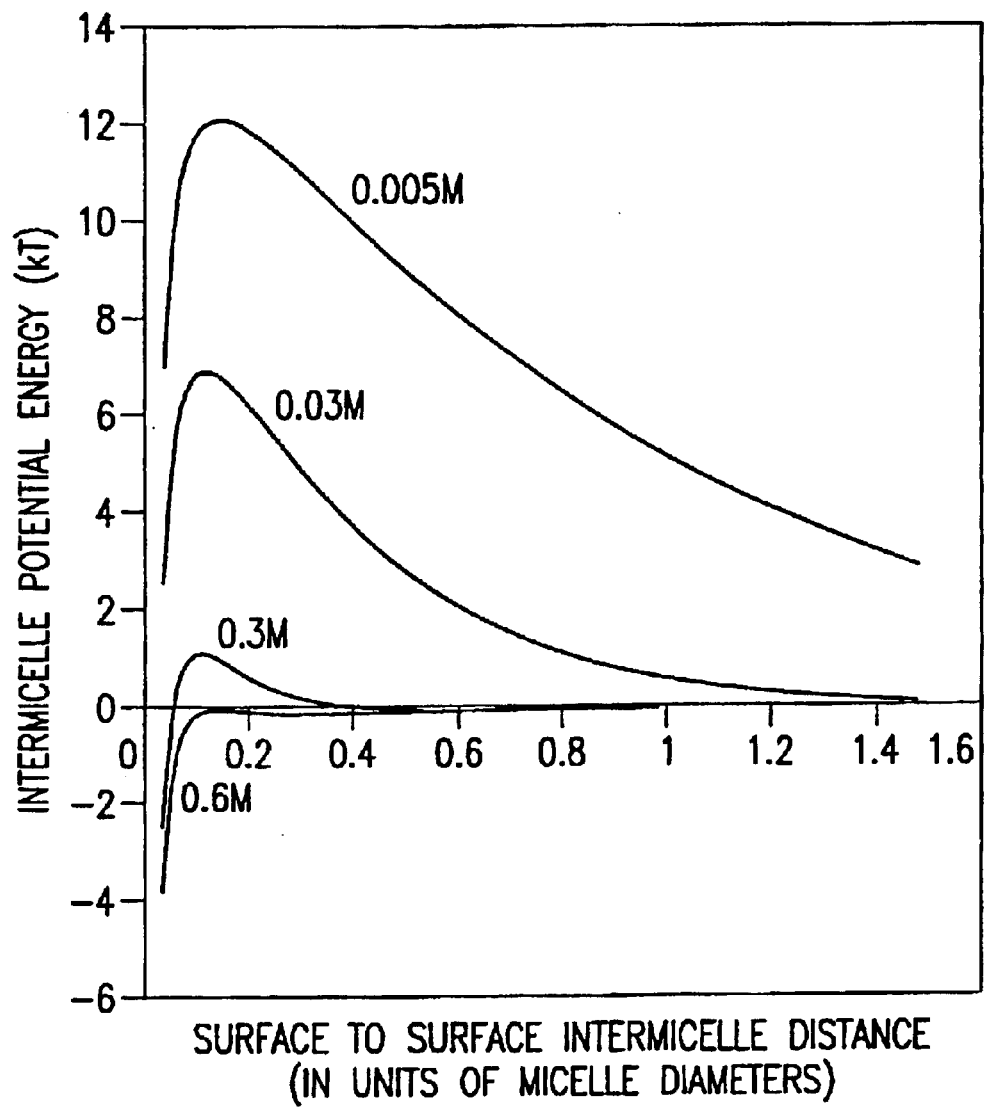
FIG. 1 is a graph showing the relationship between $V_{max}/kT$ and salt concentration.

Micelles can also grow in hydrodynamic diameter via an aggregation and fusion mechanism which is governed by particle interaction potential energy. The tendency for aggregation can be expressed as a stability ratio W. The stability of the micelles increases with W. W is inversely related to the salt concentration of the solution and directly related to the electrostatic charge of the micelle. Therefore, as the salt concentration in solution is lowered and/or the electrostatic charge of the micelle is increased, the stability of the micelles is increased relative to growth from an aggregation-fusion mechanism. FIG. 1 shows how, at salt concentrations greater than 0.6 M, the maximum interaction potential energy ($V_{max}$) between micelles is zero and the aggregation rate is only diffusion limited. As the salt concentration is decreased, however, $V_{max}/kT$ increases and the aggregation rate decreases accordingly. Therefore, salt concentration can be adjusted to impart the necessary stability to the system.

To attain the desired micelle hydrodynamic diameter using an acidic amphiphilic compound, the acidic amphiphilic compound is dissolved in an aqueous alkaline solution at a predetermined pH value and a constant metal ion concentration. The pH must be higher than the pKa of the at least one ionizable group of the acidic amphiphilic compound. The aqueous alkaline solution is prepared by adding at least one basic metal salt, at least one neutral metal salt, and a predetermined metal ion concentration to an aqueous solution. Preferably the basic metal salt and the neutral metal salt have the same metal ion. Typical metal ions include, without limitation, $Ca^{2+}$, $Mg^{2+}$, $Ba^{2+}$, $Fe^{2+}$, $Fe^{3+}$, $Al^{3+}$, $Mn^{3+}$, $Mn^{2+}$, $Zn^{2+}$, $Cu^{2+}$, $Cu^+$, $Ni^{2+}$, $Sn^{2+}$, $Na^+$, $Li^+$, $K^+$ and the like. Preferred metal ions include $Na^+$, $K^+$, $Li^+$, $Ca^{2+}$, $Ba^+$, $Mg^{2+}$, and $Al^{3+}$. Typical basic metal salts useful in the present invention are, for example, the oxide and hydroxide salts of the aforementioned metal ions. Typical neutral metal salts useful in the present invention include, for example, halide salts (e.g., chloride, fluoride, bromide, iodide) of the aforementioned metal ions. Adding the acidic amphiphilic compound to the aqueous alkaline solution results in micelles with a fixed, preselected hydrodynamic diameter. "Fixed" means that the hydrodynamic diameter is stable (i.e., does not substantially change), and "preselected" means that hydrodynamic diameter was chosen for its optimal or desired pharmacokinetic and/or other properties.

To attain the desired micelle hydrodynamic diameter using a basic amphiphilic compound, the basic amphiphilic compound is dissolved in an aqueous acid solution at a predetermined pH value and a constant metal ion concentration. The pH value must be lower than the pKa of the at least one ionizable group of the basic amphiphilic compound. The aqueous acidic solution is prepared by adding at least one protic acid, at least one neutral metal salt, and a predetermined metal ion concentration to an aqueous solution. Preferably the protic acid and the neutral metal salt have the same metal ion. Typical metal ions include, without limitation, $Ca^{2+}$, $Mg^{2+}$, $Ba^{2+}$, $Fe^{2+}$, $Fe^{3+}$, $Al^{3+}$, $Mn^{3+}$, $Mn^{2+}$, $Zn^{2+}$, $Cu^{2+}$, $Cu^+$, $Ni^{2+}$, $Sn^{2+}$, $Na^+$, $Li^+$, $K^+$ and the like. Preferred metal ions includes $Na^{30}$ , $K^+$, $Li^+Ca^{2+}$, $Ba^+$, $Mg^{2+}$, and $Al^{3+}$. Typical protic acid useful in the present invention are, for example, hydrochloric acids, Phosphoric acids, sulfuric acids, acetic acids, citric acids, carbonic acids and the like. Typical neutral metal salts useful in the present invention include, for example, halide salts (e.g., chloride, fluoride, bromide, iodide) of the aforementioned metal ions. Adding the basic amphiphilic compound to the aqueous acid solution results in micelles with a fixed, preselected hydrodynamic diameter.

The concentration of the amphiphilic compound in the aqueous alkaline or acidic solution will be higher than the critical micelle concentration of the amphiphilic compound. The conditions which yield micelles of a preselected hydrodynamic diameter can be determined by preparing micelles in a matrix of pH values and salt concentrations. Different micelle hydrodynamic diameters result from the preparation of micelles in solutions with different pH values and salt concentrations. Thereafter, a solution comprising micelles with a fixed, preselected hydrodynamic diameter can be prepared based on the selected concentration of the acidic or basic amphiphilic compound, the pH, and the concentration of metal ions.

In addition to the above, the inventors have unexpectedly discovered that the hydrodynamic diameter of the micelles in the aqueous acidic or alkaline solution will remain substantially the same when the pH of the aqueous acidic or alkaline solution is neutralized (i.e., wherein ionizable groups in the amphiphilic compound are neutralized relative to the charged ionizable groups in the amphiphilic compound).

In particular, an aqueous solution comprising a buffer system and/or at least one strong acid is added to the aqueous alkaline solution comprising the micelles of the acidic amphiphilic compound in an amount sufficient to produce an aqueous solution having a neutral pH relative to the pH of the aqueous alkaline solution. The hydrodynamic diameter of the micelles in the aqueous solution having the relatively neutral pH will remain substantially the same as the hydrodynamic diameter of the micelles in the aqueous alkaline solution.

In another embodiment, an aqueous solution comprising a buffer system and/or at least one strong base is added to the aqueous acid solution comprising the micelles of the basic amphiphilic compound in an amount sufficient to produce an aqueous solution having a neutral pH relative to the pH of the aqueous acidic solution. The hydrodynamic diameter of the micelles in the aqueous solution having the relatively neutral pH will remain substantially the same as the hydrodynamic diameter of the micelles in the aqueous acid solution.

In the present invention, the terms "basic" or "alkaline" pH and "neutral" pH are relative terms. For example, when the first aqueous solution has a basic or alkaline pH, and the final aqueous solution has a neutral pH, the neutral pH is neutral relative to the pH of the basic or alkaline solution. In other words, the pH of the neutral solution is lower than the pH of the alkaline solution. More preferably, when the first aqueous solution has a basic or alkaline pH, the pH is from about 9 to about 13, more preferably from about 10 to about 12. Relative to the first alkaline solution, the neutral pH is preferably from about 4 to less than 9, more preferably from about 6 to less than 9, even more preferably from about 7 to less than 9, still more preferably from about 7 to about 8, most preferably about 7.4 to about 7.6.

Similarly, the terms "acidic" pH and "neutral" pH are relative terms. For example, when the first aqueous solution has an acidic pH, and the final aqueous solution has a neutral pH, the neutral pH is neutral relative to the pH of the acidic solution. In other words, the pH of the neutral solution is higher than the pH of the acidic solution. More preferably, when the first aqueous solution has an acidic pH, the pH is from about 1 to about 6, more preferably from about 3 to about 5. Relative to the first acidic solution, the neutral pH is preferably more than 6 to about 13, more preferably from about 7 to about 9, still more preferably from about 7 to about 8, most preferably about 7.4 to about 7.6.

When the hydrodynamic diameter of the micelles in the aqueous solution having the relatively neutral pH remains "substantially the same" as the hydrodynamic diameter of the micelles in the aqueous alkaline or acidic solution, "substantially the same" means that the hydrodynamic diameter of the micelles in the relatively neutral solution does not change by more than 4 nm, more preferably does not change by more than 2 nm, still more preferably does not change by more than 1 nm, even more preferably does not change by more than 0.5 nm, and most preferably does not change at all from the hydrodynamic diameter of the micelles in the alkaline or acidic solution.

The buffer system may be any known in the art including, for example, phosphate buffers, acetate buffers, citrate buffers, maleate buffers, carbonate buffers, bicarbonate buffers, tartrate buffers, tromethamine buffers, triethanolamine buffers, meglumine buffers and the like. The strong acid can by any known in the art including, for example, hydrochloric acid, sulfuric acid, phosphoric acid and the like. The strong base can be any known in the art including, for example, sodium hydroxide, potassium hydroxide and the like.

The hydrodynamic diameter of the micelles of the present invention can be from about 1 nm to about 100 nm, preferably from about 5 nm to about 50 nm, more preferably from about 6 nm to about 20 nm, even more preferably from about 7 nm to about 15 nm, and most preferably from about 7 nm to about 9 nm.

The hydrodynamic diameter of micelles of the present invention preferably refers to a range of hydrodynamic diameters of about 5 nm, preferably about 4 nm, more preferably about 3 nm, most preferably about 2 nm or about 1 nm. For example, with respect to a hydrodynamic diameter range of about 2 nm, the hydrodynamic diameter can be from about 7 nm to about 9 nm. Alternatively, the hydrodynamic diameter can be from about 2 nm to about 4 nm; or from about 3 nm to about 5 nm; or from about 4 nm to about 6 nm; or from about 5 nm to about 7 nm; or from about 6 nm to about 8 nm; or from about 8 nm to about 10 nm; or from about 9 nm to about 11 nm; or from about 10 nm to about 12 nm; or from about 11 nm to about 13 nm; or from about 12 nm to about 14 nm; or from about 13 nm to about 15 nm; or from about 14 nm to about 16 nm; or from about 15 nm to about 17 nm; or from about 16 nm to about 18 nm; or from about 17 nm to about 19 nm; or from about 18 nm to about 20 nm; or from about 19 nm to about 21 nm; or from about 20 nm to about 22 nm; or from about 21 nm to about 23 nm; or from about 22 nm to about 24 nm; or from about 23 nm to about 25 nm; or from about 24 nm to about 26 nm. In other words, the 2 nm range (or the 5 nm range or the 4 nm range or the 3 nm range or the 1 nm range) can be anywhere in the range of from about 1 nm to about 100 nm; preferably from about 5 nm to about 50 nm, more preferably from about 6 nm to about 20 nm, even more preferably from about 7 nm to about 15 nm, and most preferably from about 7 nm to about 9 nm.

The hydrodynamic diameter of micelles also means that substantially all the micelles have about the same hydrodynamic diameter (i.e., or range of hydrodynamic diameters as described above). "Substantially all the micelles have about the same hydrodynamic diameter" generally means that more than 50% of the micelles have a hydrodynamic diameter that falls within the range as described above; preferably more than 60%, 70% or 80% of the micelles have a hydrodynamic diameter that falls within the range as described above; even more preferably about 90%, about 95%, or about 99% of the micelles have a hydrodynamic diameter that falls within the range as described above; most preferably 100% of the micelles have a hydrodynamic diameter that falls within the range as described above.

Acidic or basic amphiphilic compounds for use in the present invention include any acidic or basic amphiphilic compound known in the art. Preferably the acidic or basic amphiphilic compound comprises at least one ionizable group. The at least one ionizable group of the acidic amphiphilic compound can be, for example, phosphoric acids, carboxylic acids, sulfuric acids, sulfonic acids, sulfinic acids, thiols, alcohols, enols and the like. The at least one ionizable group of the basic amphiphilic compound can be, for example, amines, phosphines, and the like.

Exemplary acidic or basic amphiphilic compounds comprising at least one ionizable group include the compounds described in WO 96/39411 and U.S. Pat. Nos. 5,530,113, 5,681,824, 5,750,664, 5,935,938, and 6,184,366, the disclosures of which are incorporated by reference herein in their entirety. These compounds are generally represented by Formula (A), pharmaceutically acceptable salts thereof, and/or stereoisomers (including enantiomers and/or diastereomers) thereof:

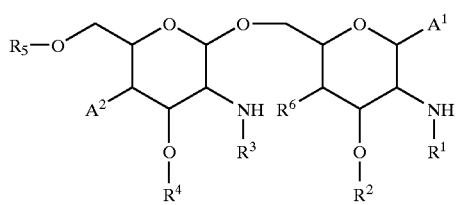
(A)

wherein R¹ is selected from the group consisting of:

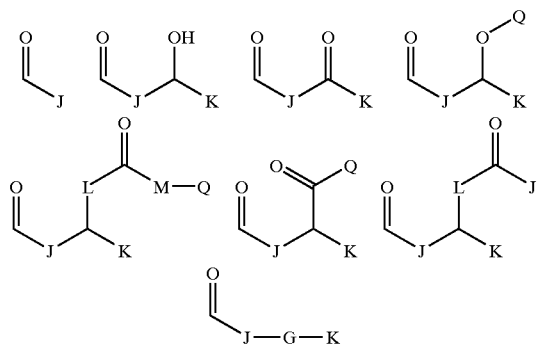

J, K and Q are each independently a straight or branched $C_{1-15}$ alkyl;
L is O, N or C;
M is O or N;
G is N, O, S, SO or $SO_2$;
R² is a straight or branched $C_{5-15}$ alkyl;
R³ is selected from the group consisting of:

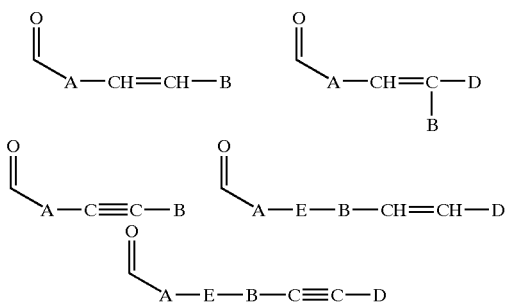

E is N, O, S, SO or $SO_2$;

A, B and D are each independently a straight or branched $C_{1-15}$ alkyl group;
R⁴ is a straight or branched $C_{4-20}$ alkyl group or

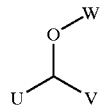

U and V are each independently a straight or branched $C_{2-15}$ alkyl group;
W is a hydrogen or a straight or branched $C_{1-5}$ alkyl group;
R⁵ is hydrogen, —J', —J'—OH, —J'—O—K', —J'—O—K'—OH or J'—O—PO(OH)₂;
J' and K' are each independently a straight or branched $C_{1-5}$ alkyl group;
R⁶ is hydroxy, halogen, a $C_{1-5}$ alkoxy group or a $C_{1-5}$ acyloxy group;
A¹ and A² are each independently selected from the group consisting of:

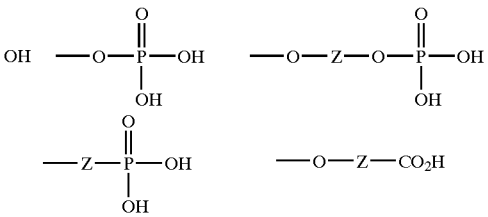

Z is a straight or branched $C_{1-10}$ alkyl group.

The term "alkyl" refers to aliphatic organic groups which may be branched or straight and which may optionally be substituted with one or more halogen atoms at any position along the alkyl chain. The term "pharmaceutically acceptable salt" includes salts of compounds derived from the combination of the compound and an organic or inorganic acid or base. Exemplary pharmaceutically acceptable salts include lysine salts, tris salts, ammonium salts, sodium salts and the like.

A preferred compound of Formula (A) is Compound (1), pharmaceutically acceptable salts thereof, and/or stereoisomers (including enantiomers and/or diastereomers) thereof:

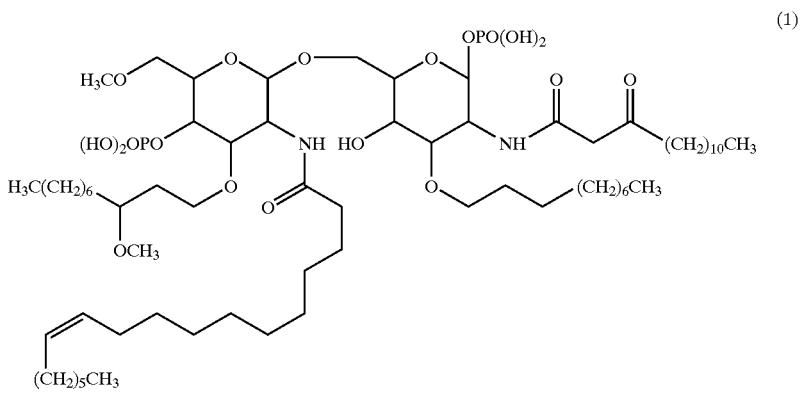

(1)

In a preferred embodiment, Compound (1) is Compound (1A) or a pharmaceutically acceptable salt thereof, which is represented by the following formula:

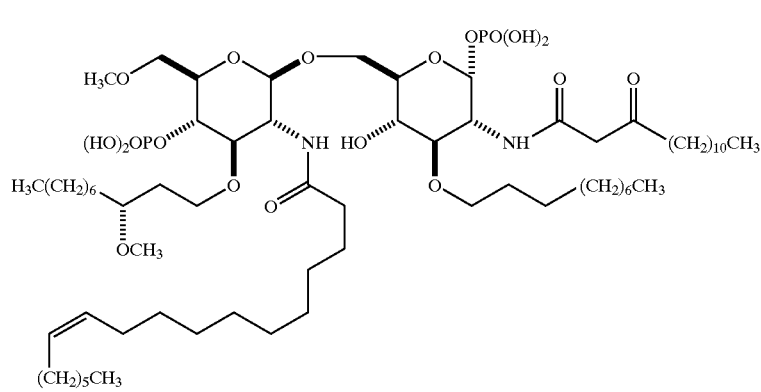

(1A)

When Compound 1A is a sodium salt (i.e., both hydrogen atoms in both —OPO(OH)$_2$ groups are replaced with sodium), then the compound is E5564.

Other preferred compounds described in WO 96/39411 and U.S. Pat. Nos. 5,530,113, 5,681,824, 5,750,664, 5,935, 938, and 6,184,366 for use in the present invention include those of Formula (B), pharmaceutically acceptable salts thereof, and/or stereoisomers (including enantiomers and/or diastereomers) thereof:

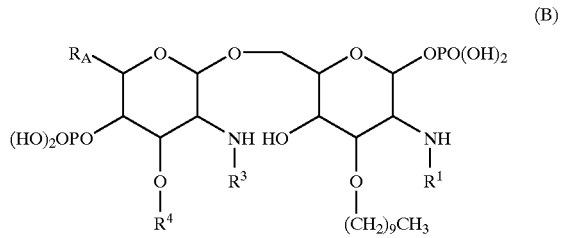

(B)

wherein $R^1$, $R^3$ and $R^4$ are as defined below:

B479, B214, B218, B231, B235, B272, B287, B294, B300, B318, B377, B380, B406, B410, B425, B426, B427, B442, B451, B452, B459, B460, B464, B465, B466, B531, B415, B718, B587, B737, B736, B725, B763, B477, B1510, and the like.

Methods for making the above compounds are described in WO 96/39411 and U.S. Pat. Nos. 5,530,113, 5,681,824, 5,750,664, 5,935,938, and 6,184,366, the disclosures of which are incorporated by reference herein in their entirety.

The lipopolysaccharides described in WO 96/39411 and U.S. Pat. Nos. 5,530,113, 5,681,824, 5,750,664, 5,935,938, and 6,184,366 are useful for treating and/or preventing any lipopolysaccharide-mediated disorder in a patient in need thereof including, for example, sepsis, septicemia (e.g., endotoxemia), endotoxemia associated with gram negative bacteria (with its accompanying symptoms of fever, generalized inflammation, disseminated intravascular coagulation, hypotension, renal dysfunction and acute renal failure, acute respiratory distress syndrome, adult respiratory distress syndrome, hepatocellular destruction and/or cardiac failure), and various forms of septic shock (e.g., endotoxic shock). The lipopolysaccharides described in these patents and publication are also useful for treating or preventing localized or systemic inflammatory response to

| # | $R^1$ | $R^3$ | $R^4$ |
|---|---|---|---|
| 1 | COCH$_2$CO(CH$_2$)$_{10}$CH$_3$ | CO(CH$_2$)$_9$CH=CH(CH$_2$)$_5$CH$_3$ | (CH$_2$)$_2$CH(OCH$_3$)(CH$_2$)$_6$CH$_3$ |
| 2 | COCH$_2$CO(CH$_2$)$_{10}$CH$_3$ | CO(CH$_2$)$_9$CH=CH(CH$_2$)$_5$CH$_3$ | (CH$_2$)$_2$CH(OH)(CH$_2$)$_6$CH$_3$ |
| 3 | COCH$_2$CO(CH$_2$)$_{10}$CH$_3$ | CO(CH$_2$)$_{16}$CH$_3$ | (CH$_2$)$_2$CH(OH)(CH$_2$)$_6$CH$_3$ |
| 4 | COCH$_2$CHOH(CH$_2$)$_{10}$CH$_3$ | CO(CH$_2$)$_9$CH=CH(CH$_2$)$_5$CH$_3$ | (CH$_2$)$_2$CH(OH)(CH$_2$)$_6$CH$_3$ |
| 5 | COCH$_2$CO(CH$_2$)$_{10}$CH$_3$ | CO(CH$_2$)$_9$CH=CH(CH$_2$)$_5$CH$_3$ | (CH$_2$)$_9$CH$_3$ |
| 6 | CO(CH$_2$)$_9$CH=CH(CH$_2$)$_5$CH$_3$ | CO(CH$_2$)$_9$CH=CH(CH$_2$)$_5$CH$_3$ | (CH$_2$)$_2$CH(OH)(CH$_2$)$_6$CH$_3$ |
| 7 | CO(CH$_2$)$_{12}$CH$_3$ | CO(CH$_2$)$_9$CH=CH(CH$_2$)$_5$CH$_3$ | (CH$_2$)$_2$CH(OH)(CH$_2$)$_6$CH$_3$ |
| 8 | COCH$_2$CH(OCH$_3$)(CH$_2$)$_{10}$CH$_3$ | CO(CH$_2$)$_9$CH=CH(CH$_2$)$_5$CH$_3$ | (CH$_2$)$_2$CH(OCH$_3$)(CH$_2$)$_6$CH$_3$ |
| 9 | COCH$_2$CH(OCH$_3$)(CH$_2$)$_{10}$CH$_3$ | CO(CH$_2$)$_9$CH=CH(CH$_2$)$_5$CH$_3$ | (CH$_2$)$_2$CH(OH)(CH$_2$)$_6$CH$_3$ |
| 10 | COCH$_2$CH(OH)(CH$_2$)$_{10}$CH$_3$ | CO(CH$_2$)$_9$CH=CH(CH$_2$)$_5$CH$_3$ | (CH$_2$)$_2$CH(OCH$_3$)(CH$_2$)$_6$CH$_3$ |
| 11 | COCH$_2$CO(CH$_2$)$_{10}$CH$_3$ | CO(CH$_2$)$_9$CH=CH(CH$_2$)$_5$CH$_3$ | (CH$_2$)$_2$CH(OCH$_3$)(CH$_2$)$_6$CH$_3$ | wherein $R_A$ in Compounds (1)–(10) is CH$_2$OCH$_3$ and $R_A$ in Compound (11) is CH$_3$.

Other specific amphiphilic compounds that can be used in the present invention include those described in U.S. Pat. No. 5,530,113, the disclosure of which is incorporated by reference herein in its entirety. Such compounds include the following exemplary lipid A analogs: B274, B276, B286, B288, B313, B314, B379, B385, B387, B388, B398, B400, infection by different types of organisms in a patient in need thereof, including gram negative bacteria, and in diseases related to translocation of gram negative bacteria or endotoxin from the gut. Together these disorders are termed systemic inflammatory response syndrome or SIRS. "Patient" includes animals, preferably mammals, more preferably humans.

The compounds described in WO 96/39411 and U.S. Pat. Nos. 5,530,113, 5,681,824, 5,750,664, 5,935,938, and 6,184, 366 are administered in dosages which provide suitable inhibition of lipopolysaccharide activation of target cells; generally, these dosages are, preferably between 0.01–50 mg/patient, more preferably, between 0.05–25 mg/patient and most preferably, between 1–12 mg/patient. Most preferably the dosages are administered over three to six days as a continuous infusion or as an intermittent dosing to obtain desired plasma concentrations. It will be understood, however, that the specific dose level for any particular patient will depend on a variety of factors including the activity of the specific compound used; the age, weight, general health, and sex of the patient being treated; the time and route of administration; the rate of excretion; other drugs which have previously been administered; and the severity of the particular disease being treated.

The micelles of the present invention and the solutions comprising micelles can be used for treating or preventing any disease or disorder that the amphiphilic compounds are known to be useful for treating or preventing. As discussed above, for example, E5564 is known to be useful for treating sepsis. In the present invention, the micelles and solutions comprising micelles are preferably administered parenterally, although other forms of administration can be used (e.g., oral, topical, transdermal, ocular). The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of endotoxemia when using E5564.

Pharmaceutical compositions containing the active ingredient may be in any form suitable for the intended method of administration. Aqueous solutions and/or suspensions of the invention contain the active materials in admixture with excipients suitable for the manufacture thereof. Such excipients include a suspending agent, such as sodium carboxymethylcellulose, methylcellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate.

The pharmaceutical compositions of the invention are preferably in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

When using a lyophilized drug product, clinicians typically reconstitute the freeze-dried preparation in physiologically acceptable solutions. It is desirable to be able to store the reconstituted solution either at room temperature or under refrigeration. Freeze-dried preparations of the micelles described herein are rehydratable with water or an aqueous dextrose solution suitable for intravenous administration, with the micelle hydrodynamic diameter distribution remaining unchanged. Such reconstituted micelle solutions can be stored at room temperature or refrigerated temperatures with no change in the micelle hydrodynamic diameter.

EXAMPLES

The following examples are for purposes of illustration only, and are not intended to limit the scope of the appended claims.

Example 1

E5564 is a lipopolysaccharide analog comprising two sugar moieties and four long chain fatty acid moieties and has a molecular weight of about 1,401. Methods for preparing E5564 are described in U.S. Pat. Nos. 5,530,113, 5,681, 824, 5,750,664, 5,935,938, and 6,184,366, and WO 96/39411, the disclosures of which are incorporated by reference herein in their entirety. E5564 drug formulations with varying micelle hydrodynamic diameters, achieved by control of the pH and concentration of counter ions (e.g., sodium), were produced as follows.

E5564 was dissolved in an NaOH solution for 60 minutes. The pH of the NaOH solution can be varied from 9 to 13 by varying the NaOH and NaCl concentrations, such that the concentration of $Na^+$ in each solution was kept constant at 0.01 M. The concentration of $Na^+$ in the solution can be in the range from about 0 to 0.6 M, preferably from about 0.001 M to about 0.6 M. The E5564/NaOH solution was then combined with a phosphate buffer solution to yield a solution with a pH of 7.5.

Figure 3:
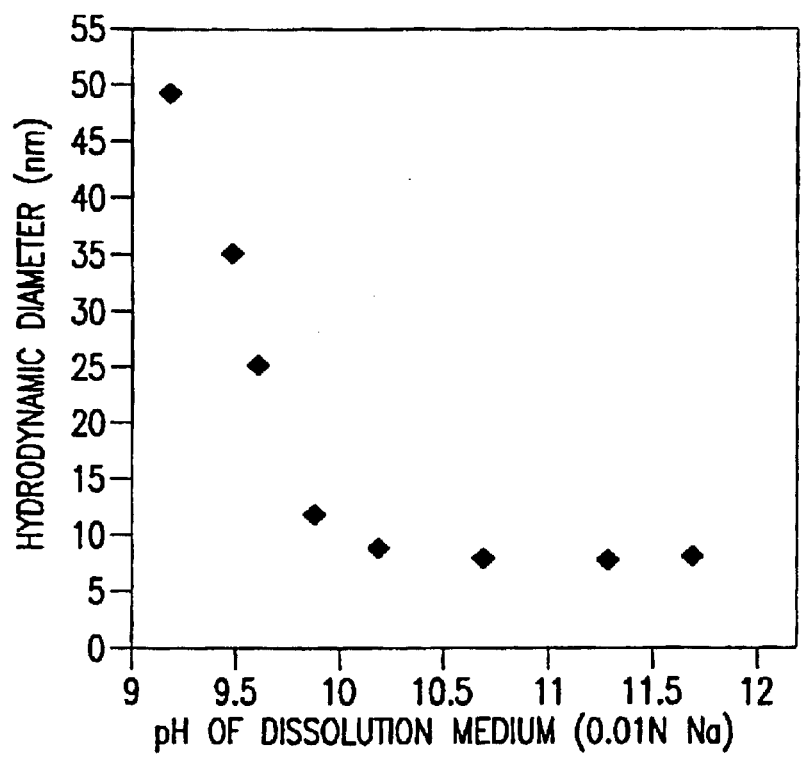
FIG. 3 is a graph showing the micelle hydrodynamic diameter for E5564 in alkaline solutions at constant sodium concentrations via the addition of NaCl.
Figure 4:
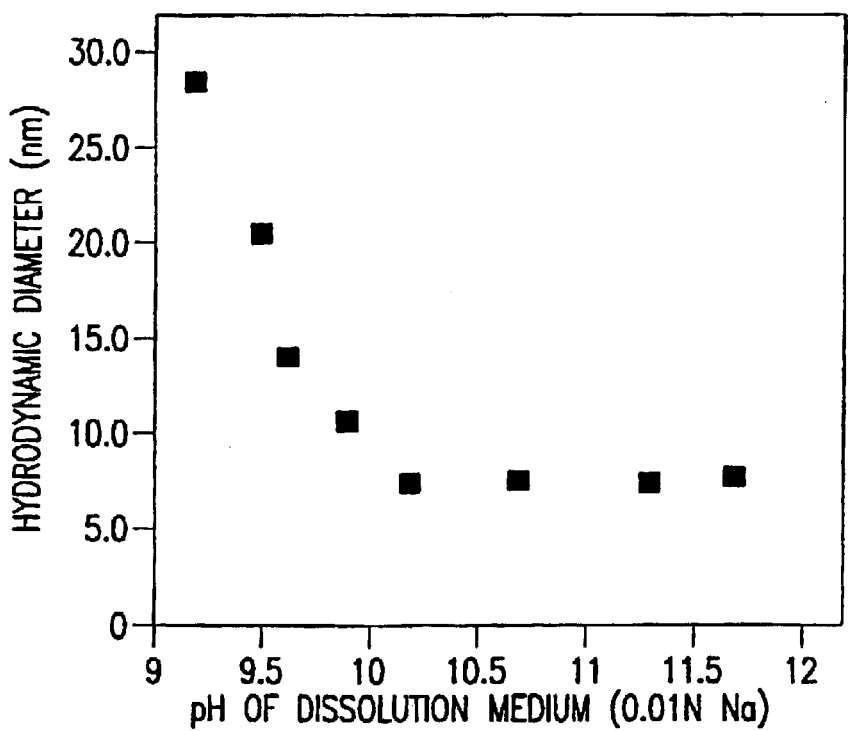
FIG. 4 is a graph showing the relationship between the micelle hydrodynamic diameter for E5564 in a phosphate buffer solution at pH 7.6 after dissolution in NaOH solutions of varying pH and constant sodium concentration (0.01 N Na).

The E5564 micelle hydrodynamic diameter was a monotonically decreasing function of pH in the alkaline solution, as shown in FIG. 3, and unexpectedly produced a micelle having a hydrodynamic diameter as small as 7 nm to 9 nm. Moreover, when the pH of the E5564 alkaline solution was adjusted to pH 7.5 by the addition of a phosphate buffer, the micelle hydrodynamic diameter unexpectedly remained the same (i.e., 7 nm to 9 nm), as shown in FIG. 4. The hydrodynamic diameter of the micelles formed was stable (i.e., fixed) under conditions useful for the manufacture and use of pharmaceutical products. Pharmaceutical preparations are often packaged in vials in a liquid or freeze-dried form. The micelles of fixed hydrodynamic diameters, prepared as described herein, were stable in a liquid or freeze-dried form.

Example 2

Micelles of E5564 having a hydrodynamic diameter of 7 nm to 9 nm (Table 1) prepared as described above were lyophilized. After lyophilization the micelles were reconstituted with water diluted in an aqueous dextrose solution (Table 2). The micelle hydrodynamic diameter of E5564 in the reconstituted solutions remained at 7 nm to 9 nm in the reconstituted physiologically acceptable solutions under various conditions. The E5564 micelle hydrodynamic diameter was stable when reconstituted in water for 24 hours at 25° C. 5564 micelle hydrodynamic diameter was unchanged after dextrose solution maintained at pH 7.4 and storage for 24 hours at 25° C. or 72 hours at 2 to 8° C. (Table 2). The E5564 micelle hydrodynamic diameter was stable as a drug protect stored in a lyophilized state at 25° C. under 60% relative humidity, or under refrigeration (Table 3). Further, the E5564 micelle hydrodynamic diameter, in micelles prepared according to the methods of the present invention, was stable under stimulated administration conditions using representative infusion equipment (Table 4).

TABLE 1

Micelle Hydrodynamic Diameter Data for E5564 Solutions Prior to Lyophilization

| sample | hydrodynamic diameter (nm) |
| --- | --- |
| 1 | 7.6 nm |
| 2 | 7.4 nm |
| 3 | 7.9 nm |

TABLE 2

Micelle Hydrodynamic Diameter of E5564 after Storage of the Reconstituted and Admixed Solutions

| sample | hydrodynamic diameter (nm) |
| --- | --- |
| immediately following reconstitution (0.5 mg/mL) | |
| sample-1 | 8.6 |
| sample-2 | 7.7 |
| sample-3 | 6.9 |
| storage for 24 hours at 25° C. | |
| sample-1 | 8.2 |
| storage for 72 hours at 2–8° C. | |
| sample-1 | 8.3 |
| immediately following admixture with 5% dextrose solution (0.14 mg/mL) | |
| sample-1 | 7.7 |
| sample-2 | 6.8 |
| storage for 24 hours at 25° C. | |
| sample-1 | 8.1 |
| storage for 72 hours at 2–8° C. | |
| sample-1 | 7.7 |

TABLE 3

Micelle Hydrodynamic Diameter of E5564 in the Reconstituted Solution after Storage of the Lyophilized Drug Product

| sample | hydrodynamic diameter (nm) |
| --- | --- |
| initial | |
| sample-1 | 8.6 |
| sample-2 | 7.7 |
| sample-3 | 6.9 |
| 6 months at 2–8° C. | |
| sample-1 | 7.5 |
| 6 months at 25° C./60% RH | |
| sample-1 | 7.3 |
| sample-2 | 7.2 |

TABLE 4

E5564 Micelle Hydrodynamic Diameter before and after a Simulated I.V. Infusion using Administration Equipment

| Administration Conditions | Mean Micelle Hydrodynamic Diameter (nm) by DLS |
| --- | --- |
| 0.5 mg/mL - control | 7.5 |
| 0.5 mg/mL - 1.4 mL/hr - 30 minutes | 7.5 |
| 0.14 mg/mL - control | 7.7 |
| 0.14 mg/mL - 5.0 mL/hr - 30 minutes | 8.7 |

The following conditions apply to the data in Table 4: Microbore 60" extension set with PVC free fluid path, No. V6212 (McGraw, Inc.); 3 cc syringe with Luer Lok, No. 309585 (Becton Dickenson); Injection site with Luer Lok, No. 2N1199 (Baxter); Needle, 20G 1, No. 305175 (Becton Dickenson); I.V. catheter, JELCO, No. 4050 (Johnson & Johnson Medical Inc.). "DLS" refers to Dynamic Light Scattering.

Example 3

Figure 2:
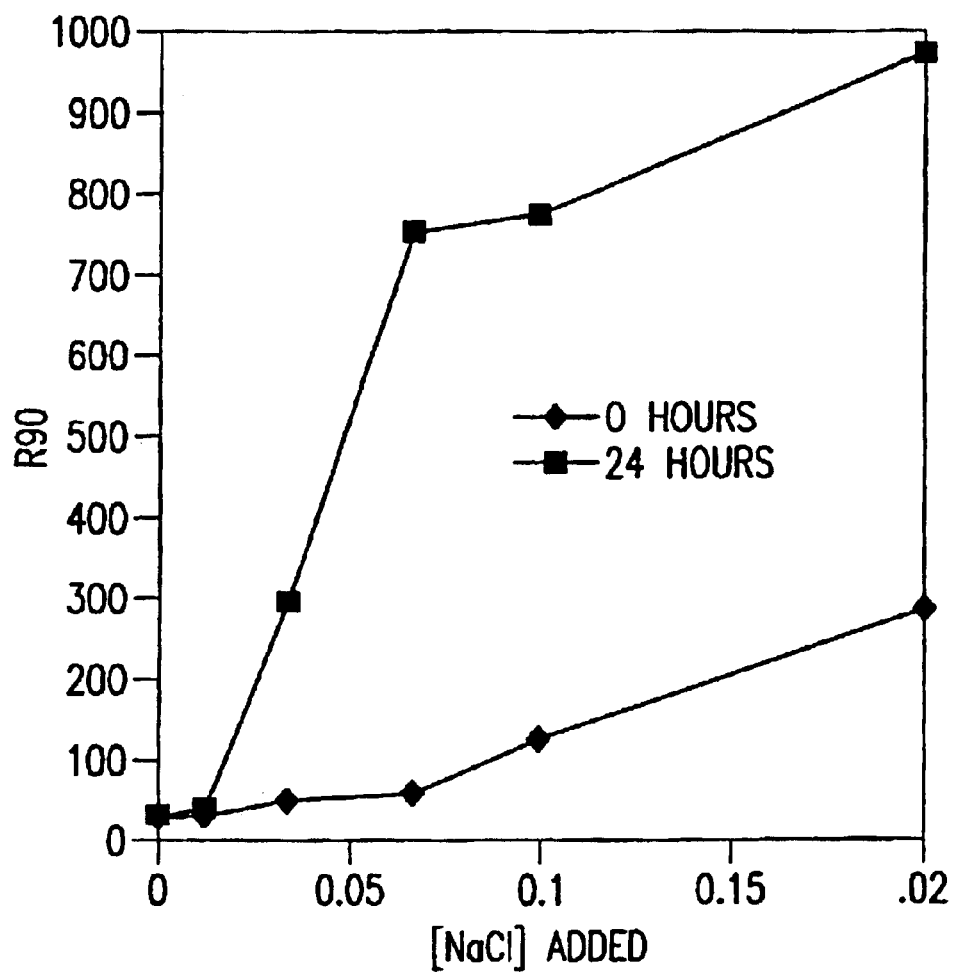
FIG. 2 is a graph showing the increase in micelle hydrodynamic diameter (as measured by an increase in light scattering intensity, R90) with added NaCl.

The micelle hydrodynamic diameter formed utilizing the methods of the invention was destabilized by added salt. FIG. 2 shows the increase in micelle hydrodynamic diameter (as measured by an increase in light scattering intensity, R90) with added NaCl. The E5564 micelle hydrodynamic diameter remained unchanged for 24 hours after addition of 0.01 M NaCl. Changes in micelle hydrodynamic diameter were observed after 24 hours with the addition of 0.03 M NaCl or greater. However, up to 0.07 M NaCl was added with no immediately appreciable change in micelle hydrodynamic diameter. Therefore, higher salt concentrations can be added if the required stability time is less than 24 hours.

Example 4

E5564 was dissolved in an aqueous sodium hydroxide solution to a pH of 10.1 to form an E5564 micelle with a hydrodynamic diameter of 7 nm. This solution was then combined with a lactose containing phosphate buffer solution to yield a solution pH of 7–8. The E5564 micelle hydrodynamic diameter in this phosphate buffer solution was 7 nm. This solution was then filtered through a 0.2 µm filter to render the solution sterile in the manner conventional to pharmaceutical manufacturing. The sterile solution was then filled into vials and freeze-dried. The micelle hydrodynamic diameter was stable upon freeze-drying. The freeze-dried product was re-hydrated with water and the E5564 micelle hydrodynamic diameter was 7 nm.

All patents, patent applications, and publications referred to herein are hereby incorporated by reference in their entirety.

Although the present invention has been set forth in detail, one skilled in the art will appreciate that changes and modifications may be made without departing from the spirit and scope of the invention or appended claims.

What is claimed is:

1. A method for preparing at least one micelle comprising Compound (1), a pharmaceutically acceptable salt thereof, and/or a stereoisomer thereof, which method comprises:

adding an amount of Compound (1), a pharmaceutically acceptable salt thereof and/or a stereoisomer thereof to a first aqueous alkaline solution comprising at least one basic metal salt, at least one neutral salt, and a predetermined concentration of metal ion; wherein Compound (1) is:

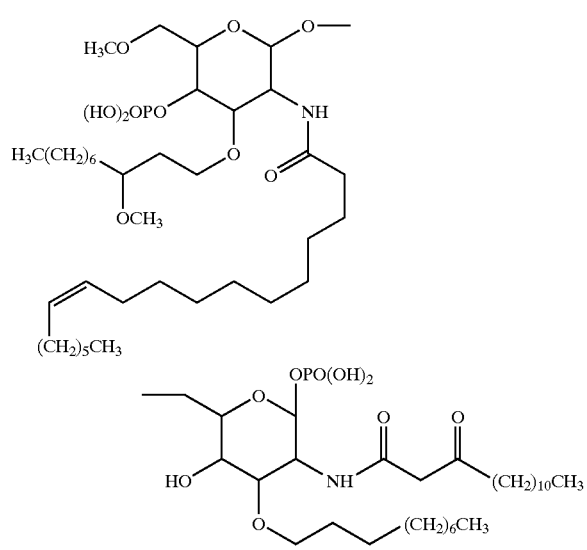

thereby forming a second aqueous alkaline solution comprising at least one micelle having a preselected hydrodynamic diameter, wherein the at least one micelle comprises Compound (1), a pharmaceutically acceptable salt thereof, and/or a stereoisomer thereof.

2. The method of claim 1, further comprising:

adding the second aqueous alkaline solution to third aqueous solution comprising a buffer system or at least one strong acid; thereby forming a fourth aqueous solution having a neutral pH relative to the pH of the second aqueous alkaline solution, wherein the fourth aqueous solution comprises at least one micelle having a preselected hydrodynamic diameter that is substantially the same as the preselected hydrodynamic diameter of the at least one micelle in the second aqueous alkaline solution; and wherein the at least one micelle in the fourth aqueous solution and the at least one micelle in the second aqueous solution comprise Compound (1), a pharmaceutically acceptable salt thereof, and/or a stereoisomer thereof.

3. The method of claim 1, wherein Compound (1) is Compound (1A) or a pharmaceutically acceptable salt thereof:

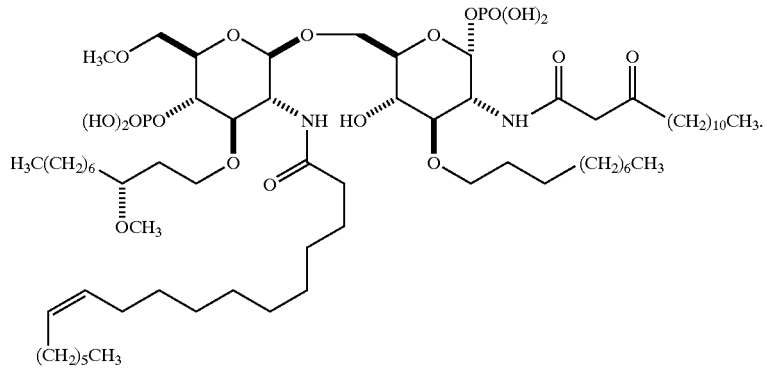

4. The method of claim 1, wherein the pH of the second aqueous alkaline solution is from about 9 to about 13; wherein the basic metal salt is NaOH; wherein the neutral metal salt is NaCl; wherein the metal ion is $Na^+$ in a concentration from about 0.001 M to about 0.01 M; and wherein the preselected hydrodynamic diameter is from about 5 nm to about 20 nm.

5. The method of claim 4, wherein the pH of the second aqueous alkaline solution is from about 10 to about 12; wherein the concentration of $Na^+$ is about 0.01 M; and wherein the preselected hydrodynamic diameter is from about 7 nm to about 9 nm.

6. The method of claim 2, wherein the pH of the fourth aqueous solution is from about 4 to less than 9; and wherein the preselected hydrodynamic diameter is from about 5 nm to about 20 nm.

7. The method of claim 6, wherein the pH of the fourth aqueous solution is from about 7 to about 8; and wherein the preselected hydrodynamic diameter is from about 7 nm to about 9 nm.

8. The method of claim 2, wherein the buffer system is a phosphate buffer system, an acetate buffer system, a citrate buffer system, a maleate buffer system, a carbonate buffer system, a bicarbonate buffer system, a tartrate buffer system, a tromethamine buffer system, a triethanolamine buffer system or a meglumine buffer system; and wherein the strong acid is one or more of hydrochloric acid, sulfuric acid or phosphoric acid.

9. A micelle produced by the method of claim 1 or claim 2.

10. A method of delivering a micelle to a patient comprising intravenously administering the micelle of claim 9 to the patient.

11. A method for treating sepsis in a patient in need thereof comprising intravenously administering an effective amount of the micelle of claim 9 to the patient.

12. An aqueous solution comprising at least one micelle prepared by the method of claim 1 or claim 2.

13. A method of delivering an aqueous solution comprising at least one micelle to a patient comprising intravenously administering the aqueous solution of claim 12 to the patient.

14. A method for treating sepsis in a patient in need thereof comprising intravenously administering an effective amount of the aqueous solution of claim 12 to the patient.

15. A micelle comprising Compound (1), a pharmaceutically acceptable salt thereof, and/or a stereoisomer thereof, wherein the micelle has a hydrodynamic diameter of about 5 nm to about 20 nm, wherein Compound (1) is:

17. A method of delivering at least one micelle to a patient comprising intravenously administering at least one micelle of claim 15 to the patient.

18. A method for treating sepsis in a patient in need thereof comprising intravenously administering an effective amount of at least one micelle of claim 15 to the patient.

19. An aqueous solution comprising at least one micelle which comprises Compound (1), a pharmaceutically acceptable salt thereof, and/or a stereoisomer thereof, wherein the micelle has a hydrodynamic diameter of about 5 nm to about 20 nm; and wherein Compound (1) is:

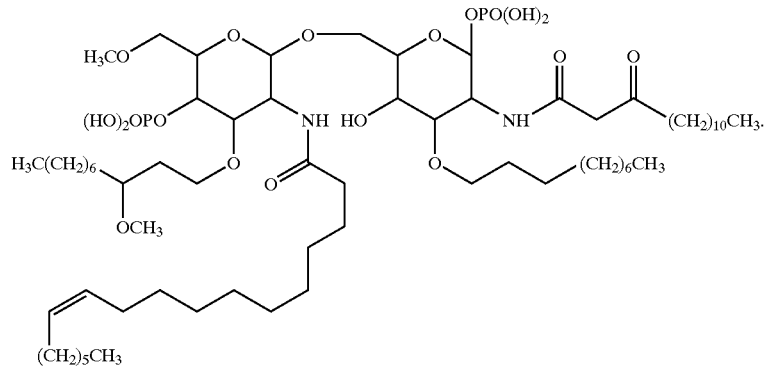

16. The micelle of claim 15, wherein Compound (1) is Compound (IA) or a pharmaceutically acceptable salt thereof:

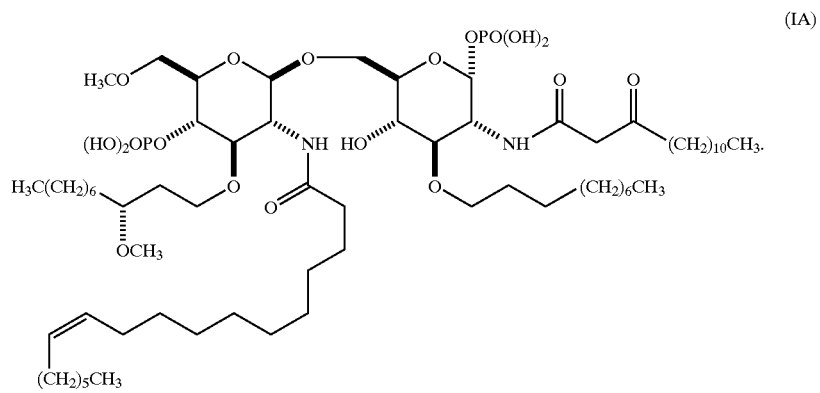

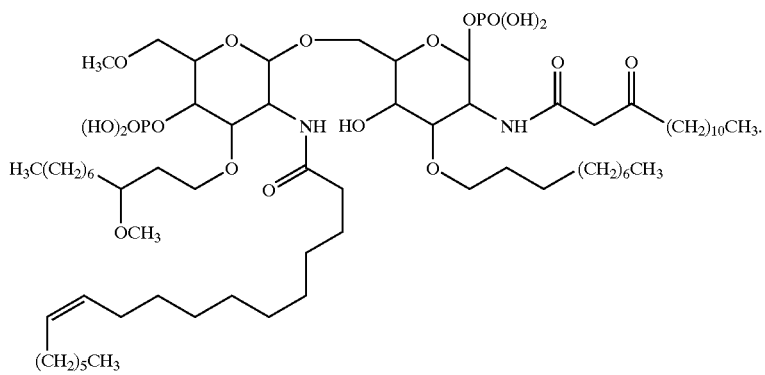

20. The aqueous solution of claim 19, wherein Compound (1) is Compound (IA) or a pharmaceutically acceptable salt thereof:

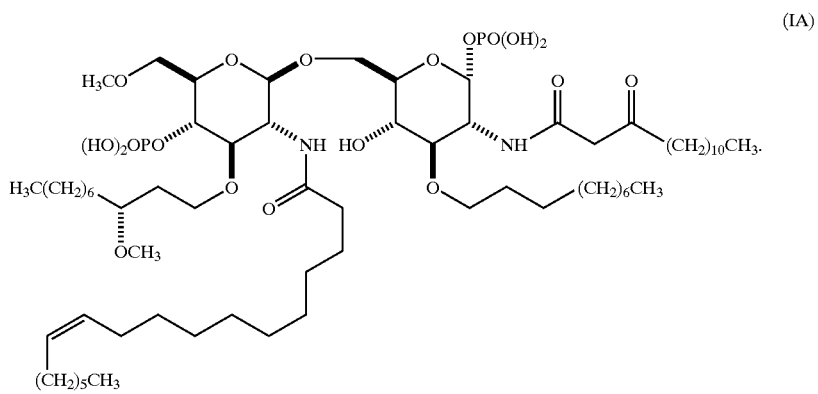

21. A method for delivering at least one micelle to a patient comprising intravenously administering the aqueous solution of claim 19 to the patient.

22. A method for treating sepsis in a patient in need thereof comprising administering an effective amount of the aqueous solution of claim 19 to the patient.

23. A method for preparing at least one micelle comprising a compound of Formula (A), a pharmaceutically acceptable salt thereof, and/or a stereoisomer thereof; wherein the method comprises:

adding an amount of Compound (A), a pharmaceutically acceptable salt thereof, and/or a stereoisomer thereof to a first aqueous alkaline solution comprising at least one basic metal salt, at least one neutral metal salt, and a predetermined concentration of metal ion; thereby forming a second aqueous alkaline solution comprising at least one micelle with a preselected hydrodynamic diameter, wherein the at least one micelle comprises a compound of Formula (A), a pharmaceutically acceptable salt thereof, and/or a stereoisomer thereof; wherein the compound of formula (A) is:

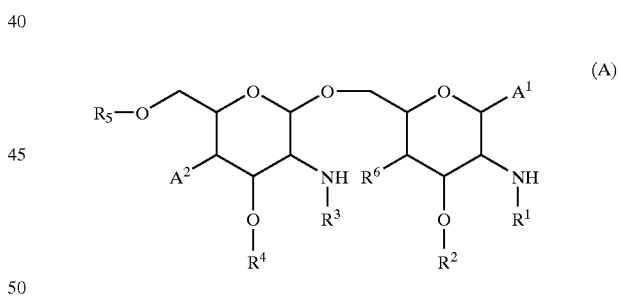

wherein $R^1$ is selected from the group consisting of:

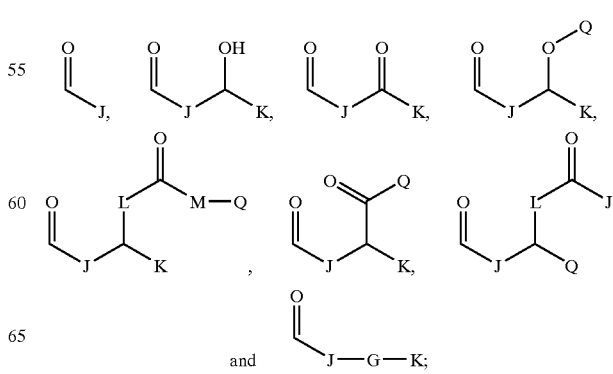

-continued

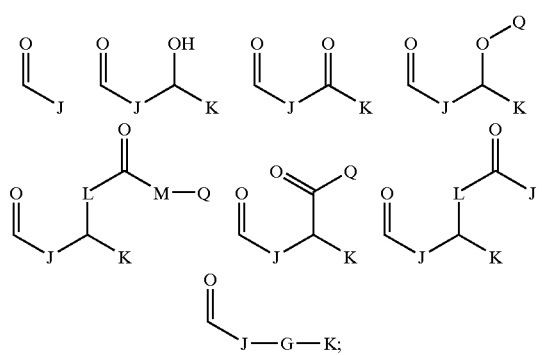

J, K and Q are each independently a straight or branched $C_{1-15}$ alkyl; L is O, N or C; M is O or N; G is N, O, S, SO or $SO_2$; $R^2$ is a straight or branched $C_{1-15}$ alkyl;

$R^3$ selected from the group consisting of:

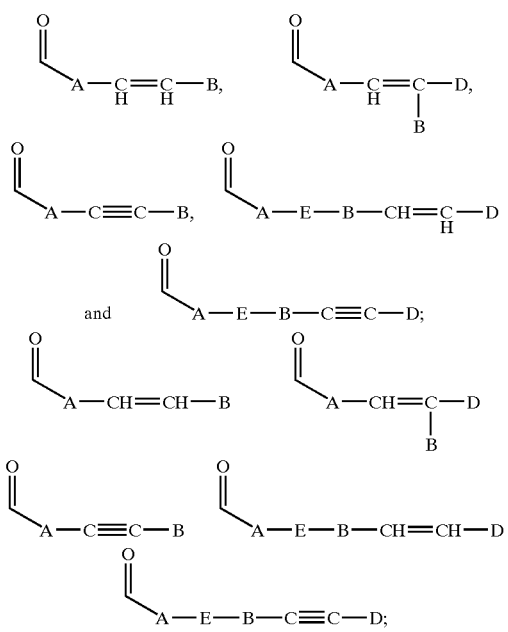

E is N, O, S, SO or $SO_2$; A, B and D are each independently a straight or branched $C_{1-15}$ alkyl group; $R^4$ is a straight or branched $C_{4-20}$ alkyl group or

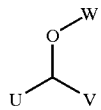

U and V are each independently a straight or branched $C_{2-15}$ alkyl group; W is a hydrogen or a straight or branched $C_{1-5}$ alkyl group; $R^5$ is hydrogen, —J', —J'—OH, —J'—O—K', —J'—O—K'—OH or J'—O—PO(OH)$_2$; J' and K' are each independently a straight or branched $C_{1-5}$ alkyl group; $R^6$ is hydroxy, halogen, a $C_{1-5}$ alkoxy group or a $C_{1-5}$ acyloxy group;

$A^1$ and $A^2$ are each independently selected from the group consisting of:

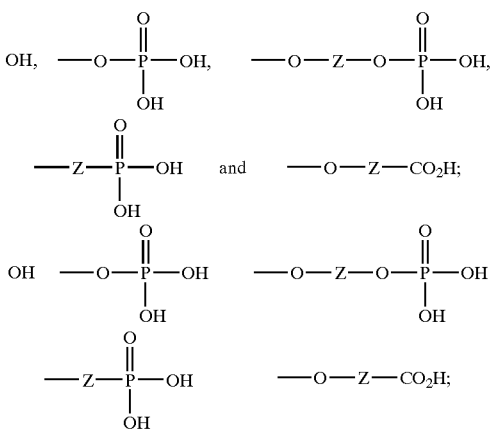

Z is a straight or branched $C_{1-10}$ alkyl group.

24. The method of claim 23, wherein the preselected hydrodynamic diameter is from about 1 nm to about 100 nm.

25. The method of claim 23, wherein the first aqueous alkaline solution has a pH from about 9 to about 13.

26. The method of claim 23, wherein the metal ion is at least one metal ion selected from the group consisting of $Ca^{2+}$, $Mg^{2+}$, $Ba^{2+}$, $Fe^{2+}$, $Fe^{3+}$, $Al^{3+}$, $Mn^{3+}$, $Mn^{2+}$, $Zn^{2+}$, $Cu^{2+}$, $Cu^+$, $Ni^{2+}$, $Sn^{2+}$, $Na^+$, $Li^+$ and $K^+$.

27. The method of claim 26, wherein the metal ion is at least one metal ion selected from the group consisting of $Na^+$, $K^+$, $Li^+$, $Ca^{2+}$, $Ba^{2+}$, $Mg^{2+}$ and $Al^{3+}$.

28. The method of claim 23, further comprising
adding the second aqueous alkaline solution to a third aqueous solution comprising a buffer system or at least one strong acid; thereby
forming a fourth aqueous solution having a neutral pH relative to the pH of the second aqueous alkaline solution, wherein the fourth aqueous solution comprises at least one micelle having a preselected hydrodynamic diameter that is substantially the same as the preselected hydrodynamic diameter of the at least one micelle in the second aqueous alkaline solution; wherein the at least one micelle in the fourth aqueous solution and the at least one micelle in the second aqueous solution comprise a compound of Formula (A), a pharmaceutically acceptable salt thereof, and/or a stereoisomer thereof.

29. The method of claim 28, wherein the neutral pH of the fourth aqueous solution is between about 4 and less than 9.

30. The method of claim 28, wherein the buffer system is a phosphate buffer system, an acetate buffer system, a citrate buffer system, a maleate buffer system, a carbonate buffer system, a bicarbonate buffer system, a tartrate buffer system, a tromethamine buffer system, a triethanolamine buffer system or a meglumine buffer system; and wherein the strong acid is at least one of hydrochloric acid, sulfuric acid and phosphoric acid.

31. The method of claim 28, further comprising lyophilizing the fourth aqueous solution.

32. A micelle produced by the method of claim 23 or claim 28.

33. A method of delivering at least one micelle to a patient comprising intravenously administering at least one micelle of claim 32 to the patient.

34. An aqueous solution comprising at least one micelle produced by the method of claim 23 or claim 28.

35. A method of delivering at least one micelle to a patient comprising intravenously administering the aqueous solution of claim 34 to the patient.

36. The method of claim 3, wherein both hydrogen atoms in both —OPO(OH)$_2$ groups in the compound of formula (IA) are replaced with sodium.

37. The micelle of claim 16, wherein both hydrogen atoms in both —OPO(OH)$_2$ groups in the compound of formula (IA) are replaced with sodium.

38. The aqueous solution of claim 20, wherein both hydrogen atoms in both —OPO(OH)$_2$ groups in the compound of formula (IA) are replaced with sodium.

39. The method of claim 2, further comprising lyophilizing the fourth aqueous solution.

40. A micelle comprising Compound (A), a pharmaceutically acceptable salt thereof, and/or a stereoisomer thereof, wherein the micelle has a hydrodynamic diameter of about 5 nm to about 100 nm; wherein Compound (A) is:

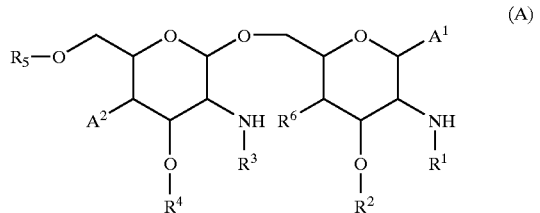

(A)

wherein R$^1$ is selected from the group consisting of:

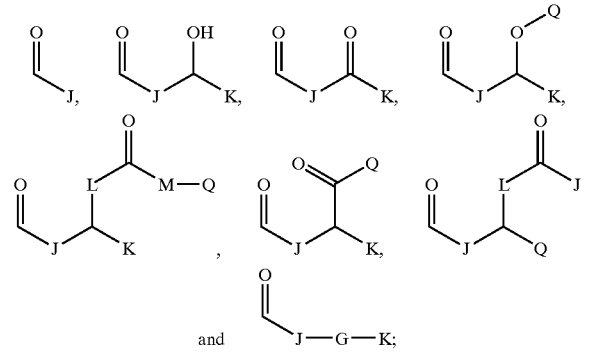

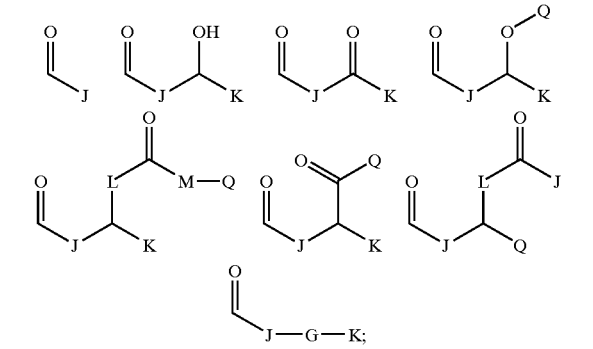

J, K and Q are each independently a straight or branched C$_{1-15}$ alkyl; L is O, N or C; M is O or N; G is N, O, S, SO or SO$_2$; R$^2$ is a straight or branched C$_{5-15}$ alkyl;

R$^3$ is selected from the group consisting of:

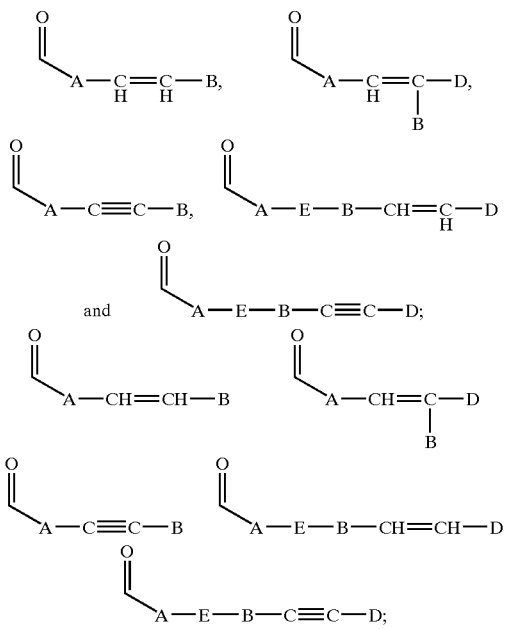

E is N, O, S, SO or SO$_2$; A, B and D are each independently a straight or branched C$_{4-20}$ alkyl group; R$^4$ is a straight or branched C$_{1-15}$ alkyl group or

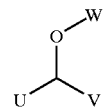

U and V are each independently a straight or branched C$_{2-15}$ alkyl group; W is a hydrogen or a straight or branched C$_{1-5}$ alkyl group; R$^5$ is hydrogen, —J', —J'—OH, —J'—O—K', —J'—O—K'—OH or J'—O—PO(OH)$_2$; J' and K' are each independently a straight or branched C$_{1-5}$ alkyl group; R$^6$ is hydroxy, halogen, a C$_{1-5}$ alkoxy group or a C$_{1-5}$ acyloxy group;

A$^1$ and A$^2$ are each independently selected from the group consisting of:

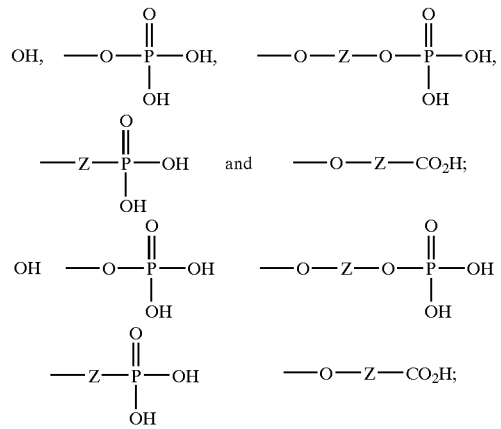

Z is a straight or branched C$_{1-10}$ alkyl group.

41. An aqueous solution comprising at least one micelle which comprises Compound (A), a pharmaceutically acceptable salt thereof, and/or a stereoisomer thereof, wherein the at least one micelle has a hydrodynamic diameter of about 5 nm to about 100 nm; wherein Compound (A) is:

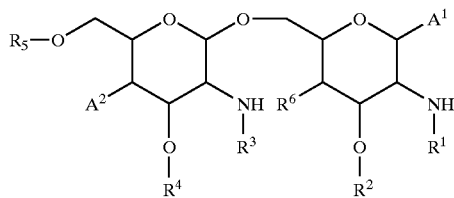

(A)

wherein $R^1$ is selected from the group consisting of:

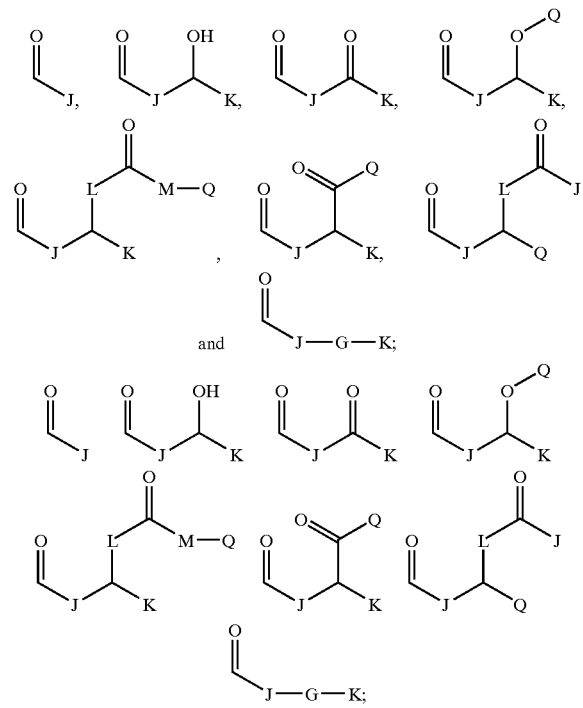

and

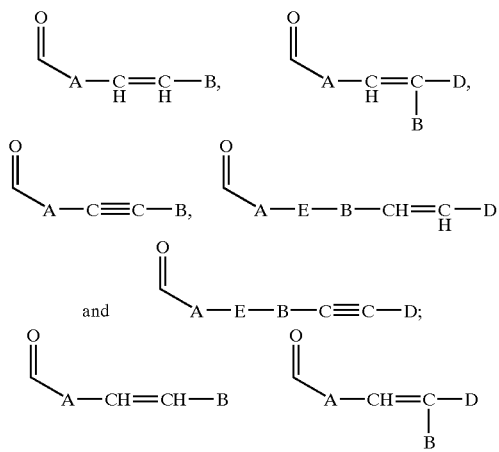

J, K and Q are each independently a straight or branched $C_{1-15}$ alkyl; L is O, N or C; M is O or N; G is N, O, S, SO or $SO_2$; $R^2$ is a straight or branched $C_{5-15}$ alkyl;

$R^3$ is selected from the group consisting of:

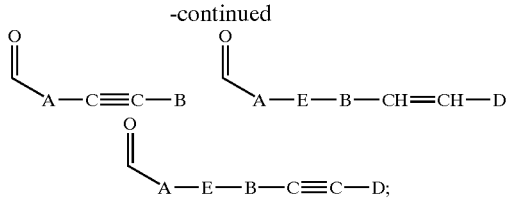

-continued

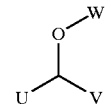

E is N, O, S, SO or $SO_2$; A, B and D are each independently a straight or branched $C_{1-15}$ alkyl group; $R^4$ is a straight or branched $C_{4-20}$ alkyl group or

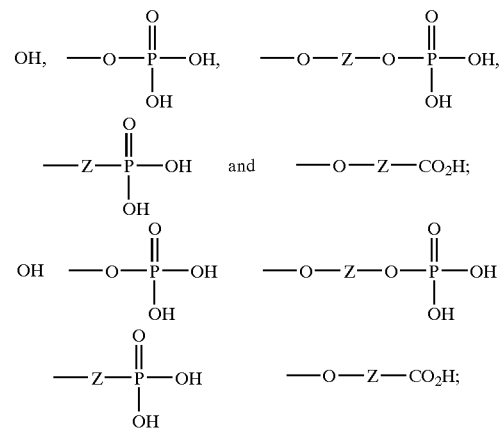

U and V are each independently a straight or branched $C_{2-5}$ alkyl group; W is a hydrogen or a straight or branched $C_{1-5}$ alkyl group; $R^5$ is hydrogen, —J', —J'—OH, —J'—O—K', —J'—O—K'—OH or J'—O—PO(OH)$_2$; J' and K' are each independently a straight or branched $C_{1-5}$ alkyl group; $R^6$ is hydroxy, halogen, a $C_{1-5}$ alkoxy group or a $C_{1-5}$ acyloxy group;

$A^1$ and $A^2$ are each independently selected from the group consisting of:

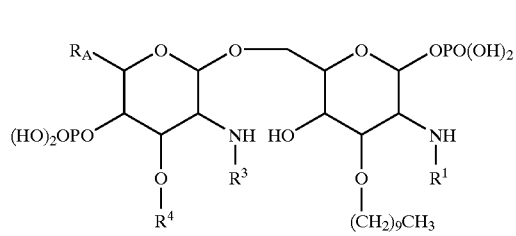

Z is a straight or branched $C_{1-10}$ alkyl group.

42. A micelle comprising Compound (B), a pharmaceutically acceptable salt thereof, and/or a stereoisomer thereof, wherein the micelle has a hydrodynamic diameter of about 5 nm to about 100 nm; wherein Compound (B) is:

(B)

wherein $R_A$ is —CH$_2$OCH$_3$; $R^1$ is —COCH$_2$CO(CH$_2$)$_{10}$CH$_3$; $R^3$ is —CO(CH$_2$)$_9$CH=CH(CH$_2$)$_5$CH$_3$; and $R^4$ is —(CH$_2$)$_2$CH(OCH$_3$)(CH$_2$)$_6$CH$_3$; wherein $R_A$ is —CH$_2$OCH$_3$; $R^1$ is —COCH$_2$CO(CH$_2$)$_{10}$CH$_3$; $R^3$ is —CO(CH$_2$)$_9$CH=CH(CH$_2$)$_5$CH$_3$; and $R^4$ is —(CH$_2$)$_2$ CH(OH)(CH$_2$)$_6$CH$_3$; wherein R$_A$ is —CH$_2$OCH$_3$; R$^1$ is COCH$_2$CO(CH$_2$)$_{10}$CH$_3$; R$^3$ is CO(CH$_2$)$_{16}$CH$_3$; and R$^4$ is —(CH$_2$)$_2$CH(OH)(CH$_2$)$_6$CH$_3$; wherein R$_A$ is —CH$_2$OCH$_3$; R$^1$ is —COCH$_2$CHOH(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$; wherein R$_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_9$CH$_3$; wherein R$_A$ is —CH$_2$OCH$_3$; R$^1$ is —CO(CH$_2$)$_9$CH=CH(CH$_2$)$_5$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$; wherein R$_A$ is —CH$_2$OCH$_3$; R$^1$ is —CO(CH$_2$)$_{12}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$; wherein R$_A$ is —CH$_2$OCH$_3$; R$^1$ is —COCH$_2$CH(OCH$_3$)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$; wherein R$_A$ is —CH$_2$OCH$_3$; R$^1$ is —COCH$_2$CH(OCH$_3$)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$; wherein R$_A$ is —CH$_2$OCH$_3$; R$^1$ is —COCH$_2$CH(OH)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$; or wherein R$_A$ is CH$_3$; R$^1$ is COCH$_2$CO(CH$_2$)$_{10}$CH$_3$; R$^3$ is CO(CH$_2$)$_9$CH=CH(CH$_2$)$_5$CH$_3$; and R$^4$ is CH$_2$)$_2$CH(OCH$_3$)(CH$_2$)$_6$CH$_3$.

43. An aqueous solution comprising at least one micelle which comprises Compound (B), a pharmaceutically acceptable salt thereof, and/or a stereoisomer thereof, wherein the at least one micelle has a hydrodynamic diameter of about 5 nm to about 100 nm; wherein Compound (B) is:

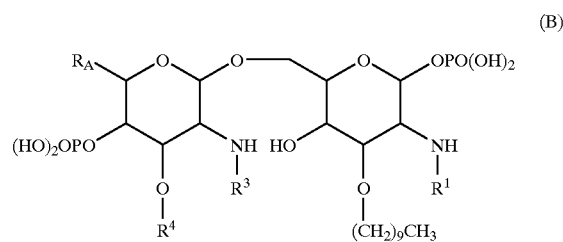

(B)

wherein R$_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$; wherein R$_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$; wherein R$_A$ is —CH$_2$OCH$_3$; R$^1$ is COCH$_2$CO(CH$_2$)$_{10}$CH$_3$; R$^3$ is CO(CH$_2$)$_{16}$CH$_3$; and R$^4$ is —(CH$_2$)$_2$CH(OH)(CH$_2$)$_6$CH$_3$; wherein R$_A$ is —CH$_2$OCH$_3$; R$^1$ is —COCH$_2$CHOH(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$; wherein R$_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_9$CH$_3$; wherein R$_A$ is —CH$_2$OCH$_3$; R$^1$ is —CO(CH$_2$)$_9$CH=CH(CH$_2$)$_5$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$; wherein R$_A$ is —CH$_2$OCH$_3$; R$^1$ is —CO(CH$_2$)$_{12}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$; wherein R$_A$ is —CH$_2$OCH$_3$; R$^1$ is —COCH$_2$CH(OCH$_3$)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$; wherein R$_A$ is —CH$_2$OCH$_3$; R$^1$ is —COCH$_2$CH(OCH$_3$)(CH$_2$)$_{10}$CH$_3$; R$^3$ is —CO(CH$_2$)$_9$CH=CH(CH$_2$)$_5$CH$_3$; and R$^4$ —(CH$_2$)$_2$CH(OH)(CH$_2$)$_6$CH$_3$; wherein R$_A$ is —CH$_2$OCH$_3$; R$^1$ is —COCH$_2$CH(OH)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH (OCH$_3$)(CH$_2$)$_6$CH$_3$; or wherein R$_A$ is CH$_3$; R$^1$ is COCH$_2$CO (CH$_2$)$_{10}$CH$_3$; R$^3$ is CO(CH$_2$)$_9$CH=CH(CH$_2$)$_5$CH$_3$; and R$^4$ CH$_2$)$_2$CH(OCH$_3$)(CH$_2$)$_6$CH$_3$.

44. A pharmaceutical formulation comprising a therapeutically effective amount of at least one micelle having a hydrodynamic diameter from about 1 nm to about 100 nm, wherein the at least one micelle comprises a compound of formula (I), a pharmaceutically acceptable salt thereof, and/or a stereoisomer thereof; wherein the compound of formula (I) is:

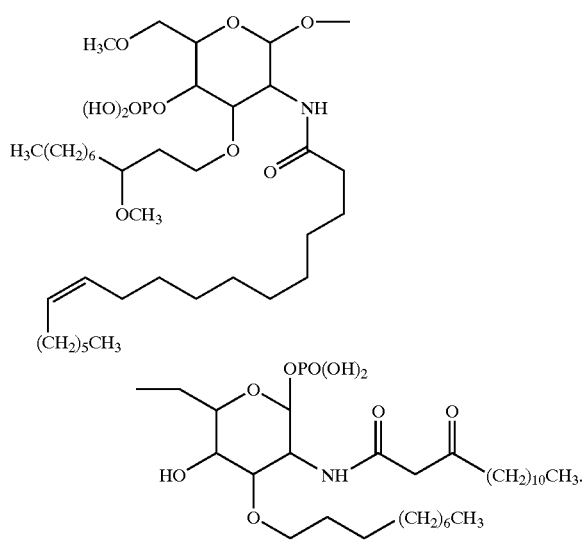

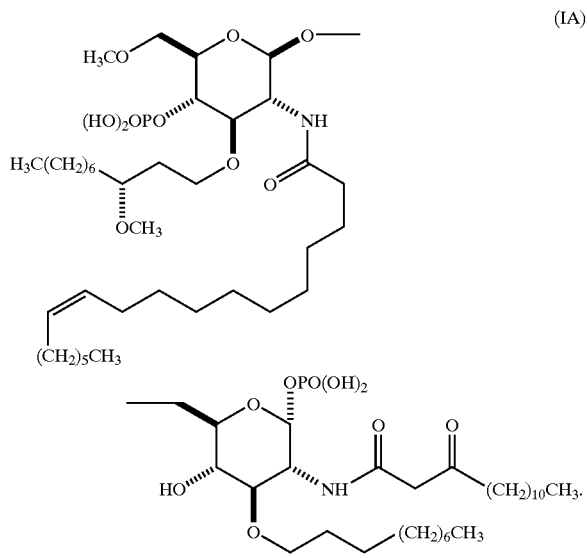

45. The pharmaceutical formulation of claim 44, wherein the compound of formula (I) is a compound of formula (IA) or a pharmaceutically acceptable salt thereof; wherein the compound of formula (IA) is:

(IA)

46. The pharmaceutical formulation of claim 45, wherein both hydrogen atoms in both —OPO(OH)$_2$ groups in the compound of formula (IA) are replaced with sodium.

47. The pharmaceutical formulation of claim 44, wherein the at least one micelle has a hydrodynamic diameter from about 5 nm to about 50 nm.

48. The pharmaceutical formulation of claim 44, wherein the at least one micelle has a hydrodynamic diameter from about 6 nm to about 20 nm.

49. The pharmaceutical formulation of claim 44, wherein the at least one micelle has a hydrodynamic diameter from about 7 nm to about 15 nm.

50. The pharmaceutical formulation of claim 44, wherein the at least one micelle has a hydrodynamic diameter from about 7 nm to about 9 nm.

51. A method for treating sepsis in a patient in need thereof comprising administering a therapeutically effective amount of the pharmaceutical formulation of claim 44, to the patient.

52. A method for treating endotoxemia in a patient in need thereof comprising administering a therapeutically effective amount of the pharmaceutical formulation of claim 44 to the patient.

53. A method for treating at least one symptom of endotoxemia associated with gram negative bacteria in a patient in need thereof comprising administering a therapeutically effective amount of the pharmaceutical formulation of claim 44 to the patient.

54. The method of claim 53, wherein the at least one symptom is selected from the group consisting of fever, inflammation, disseminated intravascular coagulation, hypotension, renal dysfunction, acute renal failure, acute respiratory distress syndrome, adult respiratory distress syndrome, hepatocellular destruction and cardiac failure.

55. A method for treating septic shock in a patient in need thereof comprising administering a therapeutically effective amount of the pharmaceutical formulation of claim 44 to the patient.

56. A method for treating systemic inflammatory response syndrome in a patient in need thereof comprising administering a therapeutically effective amount of the pharmaceutical formulation of claim 44 to the patient.

57. A pharmaceutical formulation comprising a therapeutically effective amount of at least one micelle, having a hydrodynamic diameter from about 1 nm to about 100 nm, wherein the at least one micelle comprises a compound of formula (A), a pharmaceutically acceptable salt thereof, and/or a stereoisomer thereof; wherein the compound of formula (A) is:

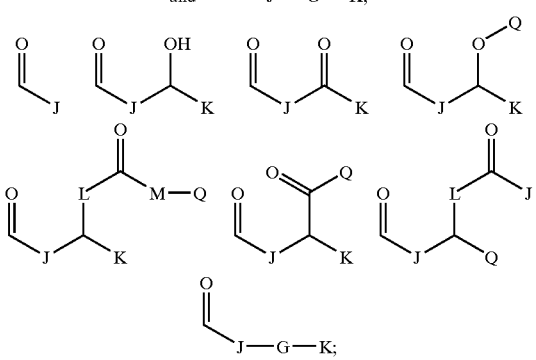

(A)

wherein $R^1$ is selected from the group consisting of:

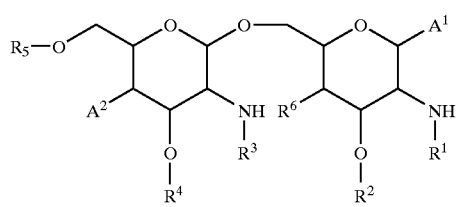

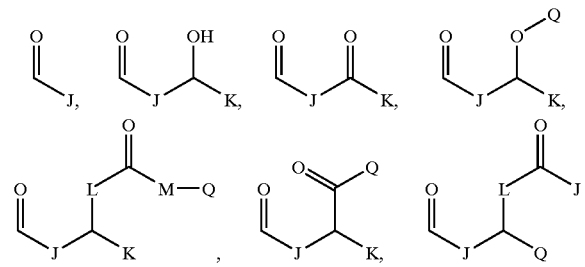

$J$, $K$ and $Q$ are each independently a straight or branched $C_{1-15}$ alkyl; $L$ is O, N or C; $M$ is O or N; $G$ is N, O, S, SO or $SO_2$; $R^2$ is a straight or branched $C_{5-15}$ alkyl;

$R^3$ is selected from the group consisting of:

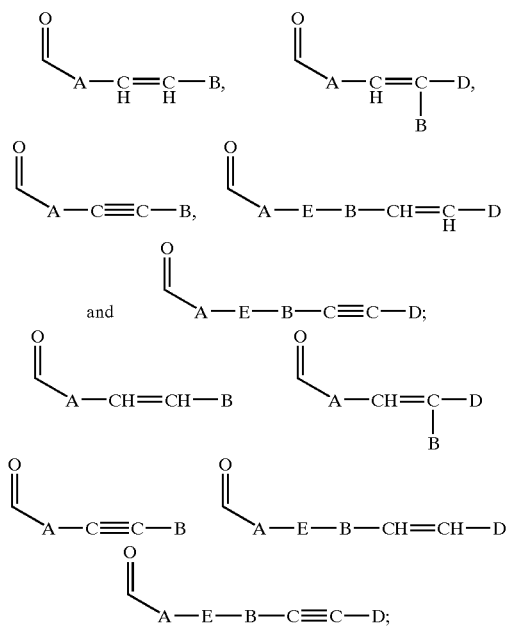

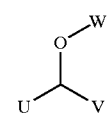

$E$ is N, O, S, SO or $SO_2$; A, B and D are each independently a straight or branched $C_{1-15}$ alkyl group; $R^4$ is a straight or branched $C_{4-20}$ alkyl group or $U$ and $V$ are each independently a straight or branched $C_{2-15}$ alkyl group; $W$ is a hydrogen or a straight or branched $C_{1-5}$ alkyl group; $R^5$ is hydrogen, —J', —J'—OH, —J'—O—K', —J'—O—K'—OH or J'—O—PO(OH)$_2$; J' and K' are each independently a straight or branched $C_{1-5}$ alkyl group; $R^6$ is hydroxy, halogen, a $C_{1-5}$ alkoxy group or a $C_{1-5}$ acyloxy group;

$A^1$ and $A^2$ are each independently selected from the group consisting of:

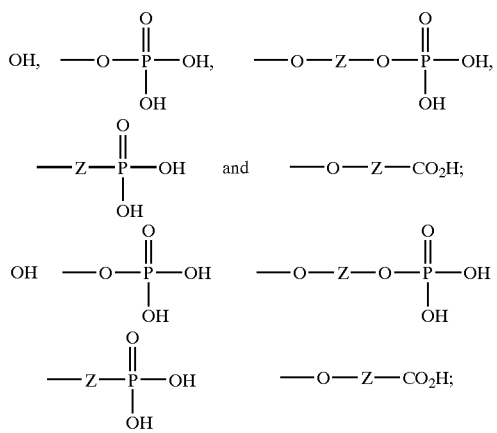

Z is a straight or branched $C_{1-10}$ alkyl group.

58. The pharmaceutical formulation of claim 57, wherein the at least one micelle has a hydrodynamic diameter from about 5 nm to about 50 nm.

59. The pharmaceutical formulation of claim 57, wherein the at least one micelle has a hydrodynamic diameter from about 6 nm to about 20 nm.

60. The pharmaceutical formulation of claim 57, wherein the at least one micelle has a hydrodynamic diameter from about 7 nm to about 15 nm.

61. The pharmaceutical formulation of claim 57, wherein the at least one micelle has a hydrodynamic diameter from about 7 nm to about 9 nm.

62. A method for treating sepsis in a patient in need thereof comprising administering a therapeutically effective amount of the pharmaceutical formulation of claim 57 to the patient.

63. A method for treating endotoxemia in a patient in need thereof comprising administering a therapeutically effective amount of the pharmaceutical formulation of claim 57 to the patient.

64. A method for treating at least one symptom of endotoxemia associated with gram negative bacteria in a patient in need thereof comprising administering a therapeutically effective amount of the pharmaceutical formulation of claim 57 to the patient.

65. The method of claim 64, wherein the at least one symptom is selected from the group consisting of fever, inflammation, disseminated intravascular coagulation, hypotension, renal dysfunction, acute renal failure, acute respiratory distress syndrome, adult respiratory distress syndrome, hepatocellular destruction and cardiac failure.

66. A method for treating septic shock in a patient in need thereof comprising administering a therapeutically effective amount of the pharmaceutical formulation of claim 57 to the patient.

67. A method for treating systemic inflammatory response syndrome in a patient in need thereof comprising administering a therapeutically effective amount of the pharmaceutical formulation of claim 57 to the patient.

68. A pharmaceutical formulation comprising a therapeutically effective amount of at least one micelle, having a hydrodynamic diameter from about 1 nm to about 100 nm, wherein the at least one micelle comprises a compound of formula (B), a pharmaceutically acceptable salt thereof, and/or a stereoisomer thereof; wherein the compound of formula (B) is:

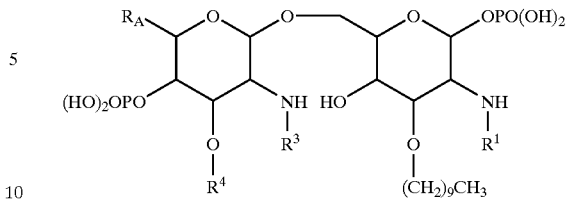

(B)

wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$; wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is $COCH_2CO(CH_2)_{10}CH_3$; $R^3$ is $CO(CH_2)_{16}CH_3$; and $R^4$ is —$(CH_2)_2CH(OH)(CH_2)_6CH_3$; wherein $R_A$ is —$CH_2OCH_3$; $R^1$ is —$COCH_2CHOH(CH_2)_{10}CH_3$; $R^3$ —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_9CH_3$; wherein $R_A$ is —$CH_2OCH_3$; $R^1$ is —$CO(CH_2)_9CH=CH(CH_2)_5CH_3$; $R^3$ is —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is —$CO(CH_2)_{12}CH_3$; $R^3$ is —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is —$COCH_2CH(OCH_3)(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$; wherein $R_A$ is —$CH_2OCH_3$; $R^1$ is —$COCH_2CH(OCH_3)(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is —$COCH_2CH(OH)(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$; or wherein $R_A$ is $CH_3$; $R^1$ is $COCH_2CO(CH_2)_{10}CH_3$; $R^3$ is $CO(CH_2)_9CH=CH(CH_2)_5CH_3$; and $R^4$ is $CH_2)_2CH(OCH_3)(CH_2)_6CH_3$.

69. The pharmaceutical formulation of claim 68, wherein the at least one micelle has a hydrodynamic diameter from about 5 nm to about 50 nm.

70. The pharmaceutical formulation of claim 68, wherein the at least one micelle has a hydrodynamic diameter from about 6 nm to about 20 nm.

71. The pharmaceutical formulation of claim 68, wherein the at least one micelle has a hydrodynamic diameter from about 7 nm to about 15 nm.

72. The pharmaceutical formulation of claim 68, wherein the at least one micelle has a hydrodynamic diameter from about 7 nm to about 9 nm.

73. A method for treating sepsis in a patient in need thereof comprising administering a therapeutically effective amount of the pharmaceutical formulation of claim 68 to the patient.

74. A method for treating endotoxemia in a patient in need thereof comprising administering a therapeutically effective amount of the pharmaceutical formulation of claim 68 to the patient.

75. A method for treating at least one symptom of endotoxemia associated with gram negative bacteria in a patient in need thereof comprising administering a therapeutically effective amount of the pharmaceutical formulation of claim 68 to the patient.

76. The method of claim 75, wherein the at least one symptom is selected from the group consisting of fever, inflammation, disseminated intravascular coagulation, hypotension, renal dysfunction, acute renal failure, acute respiratory distress syndrome, adult respiratory distress syndrome, hepatocellular destruction and cardiac failure.

77. A method for treating septic shock in a patient in need thereof comprising administering a therapeutically effective amount of the pharmaceutical formulation of claim 68 to the patient.

78. A method for treating systemic inflammatory response syndrome in a patient in need thereof comprising administering a therapeutically effective amount of the pharmaceutical formulation of claim 68 to the patient.

79. The pharmaceutical formulation of claim 44, wherein the pharmaceutical formulation is in a form that can be administered parenterally.

80. The pharmaceutical formulation of claim 57, wherein the pharmaceutical formulation is in a form that can be administered parenterally.

81. The pharmaceutical formulation of claim 68, wherein the pharmaceutical formulation is in a form that can be administered parenterally.

82. A lyophilized drug product comprising a therapeutically effective amount of at least one micelle, having a hydrodynamic diameter from about 5 nm to about 100 nm, wherein the at least one micelle comprises a compound of formula (I), a pharmaceutically acceptable salt thereof, and/or a stereoisomer thereof; wherein the compound of formula (I) is:

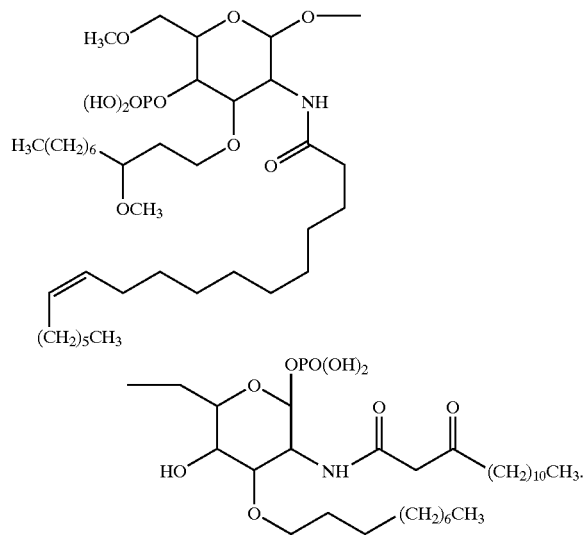

83. The lyophilized drug product of claim 82, wherein the compound of formula (I) is a compound of formula (IA) or a pharmaceutically acceptable salt thereof; wherein the compound of formula (IA) is:

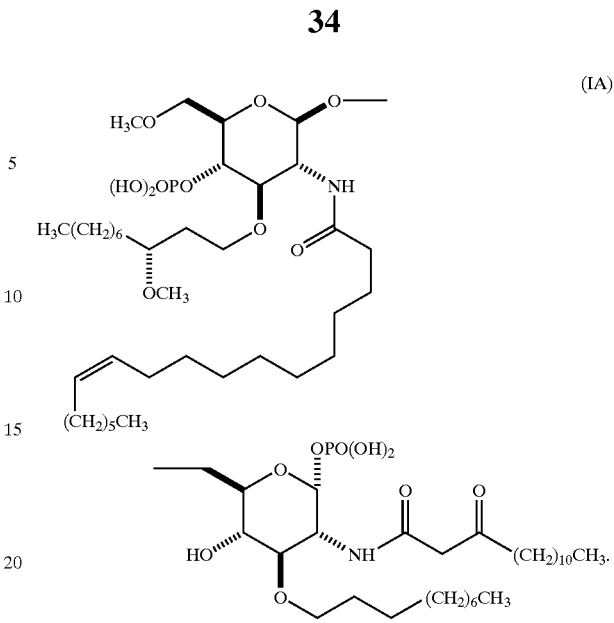

(IA)

84. The lyophilized drug product of claim 83, wherein both hydrogen atoms in both —OPO(OH)$_2$ groups in the compound of formula (IA) are replaced with sodium.

85. A lyophilized drug product comprising a therapeutically effective amount of at least one micelle, having a hydrodynamic diameter from about 5 nm to about 100 nm, wherein the at least one micelle comprises a compound of formula (A), a pharmaceutically acceptable salt thereof, and/or a stereoisomer thereof; wherein the compound of formula (A) is:

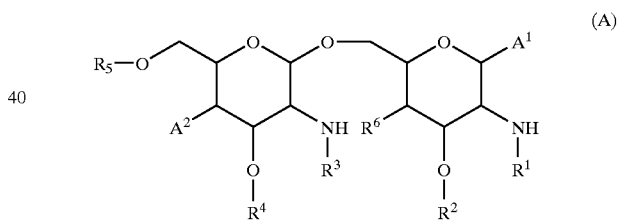

(A)

wherein $R^1$ is selected from the group consisting of:

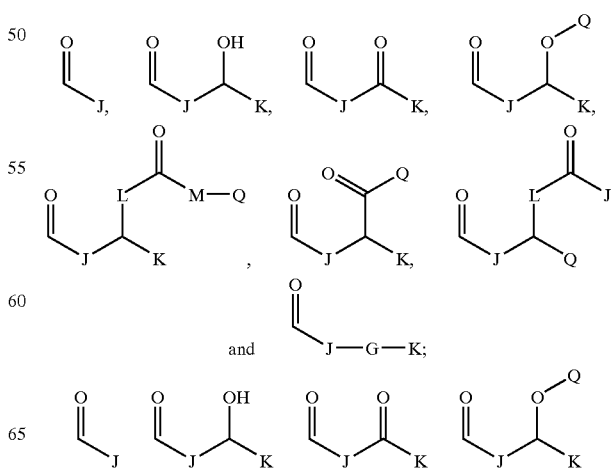

-continued

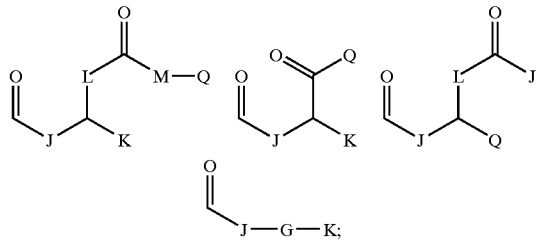

J, K and Q are each independently a straight or branched $C_{1-5}$ alkyl; L is O, N or C; M is O or N; G is N, O, S, SO or $SO_2$; $R^2$ is a straight or branched $C_{5-15}$ alkyl;

$R^3$ selected from the group consisting of:

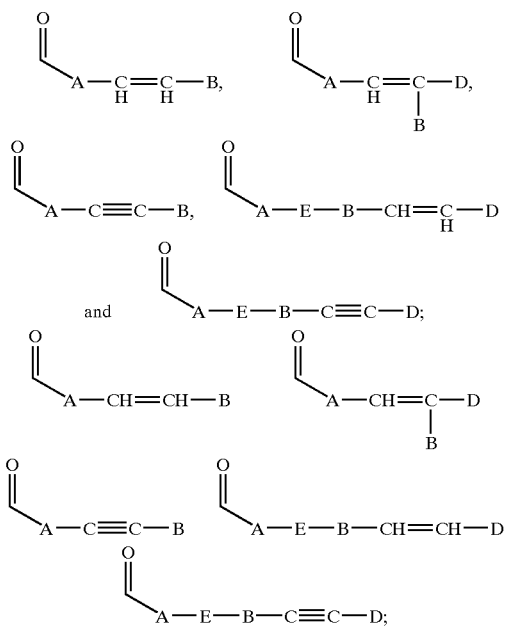

E is N, O, S, SO or $SO_2$; A, B and D are each independently a straight or branched $C_{1-5}$ alkyl group; $R^4$ is a straight or branched $C_{4-20}$ alkyl group or

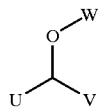

U and V are each independently a straight or branched $C_{2-15}$ alkyl group; W is a hydrogen or a straight or branched $C_{1-5}$ alkyl group; $R^5$ is hydrogen, —J', —J'—OH, —J'—O—K', —J'—O—K'—OH or J'—O—PO(OH)$_2$; J' and K' are each independently a straight or branched $C_{1-5}$ alkyl group; $R^6$ is hydroxy, halogen, a $C_{1-5}$ alkoxy group or a $C_{1-5}$ acyloxy group;

$A^1$ and $A^2$ are each independently selected from the group consisting of:

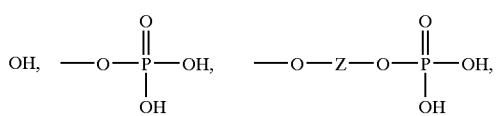

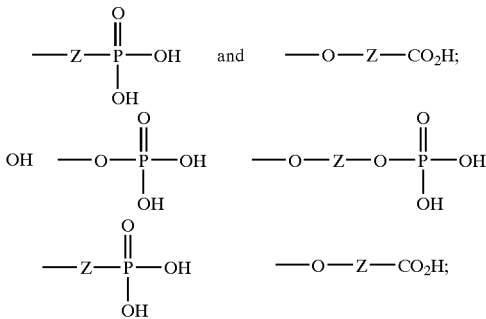

Z is a straight or branched $C_{1-10}$ alkyl group.

86. A lyophilized drug product comprising a therapeutically effective amount of at least one micelle, having a hydrodynamic diameter from about 5 nm to about 100 nm, wherein the at least one micelle comprises a compound of formula (B), a pharmaceutically acceptable salt thereof, and/or a stereoisomer thereof; wherein the compound of formula (B) is:

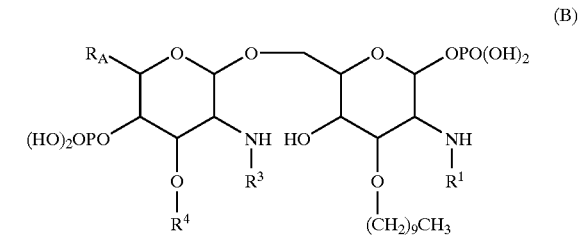

(B)

wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$; wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is $COCH_2CO(CH_2)_{10}CH_3$; $R^3$ is $CO(CH_2)_{16}CH_3$; and $R^4$ is —$(CH_2)_2CH(OH)(CH_2)_6CH_3$; wherein $R_A$ is —$CH_2OCH_3$; $R^1$ is —$COCH_2CHOH(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_9CH_3$; wherein $R_A$ is —$CH_2OCH_3$; $R^1$ is —$CO(CH_2)_9CH=CH(CH_2)_5CH_3$; $R^3$ —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is —$CO(CH_2)_{12}CH_3$; $R^3$ is —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is —$COCH_2CH(OCH_3)(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$; wherein $R_A$ is —$CH_2OCH_3$; $R^1$ is —$COCH_2CH(OCH_3)(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$; wherein $R_A$ is —$CH_2OCH_3$; $R^1$ is —$COCH_2CH(OH)(CH_2)_{10}CH_3$; $R^3$ is —$CO(CH_2)_9CH=CH(CH_2)_5CH_3R^4$ is —$(CH_2)_2CH(OCH_3)(CH_2)_6CH_3$; or wherein $R_A$ is $CH_3$; $R^1$ is $COCH_2CO(CH_2)_{10}CH_3$; $R^3$ is $CO(CH_2)_9CH=CH(CH_2)_5CH_3$; and $R^4$ is $CH_2)_2CH(OCH_3)(CH_2)_6CH_3$.

87. The method of claim 1, wherein the hydrodynamic diameter is from about 5 nm to about 100 nm.

88. The method of claim 87, wherein the hydrodynamic diameter is from about 7 nm to about 9 nm.

89. The micelle of claim 15, wherein the micelle has a hydrodynamic diameter of about 7 nm to about 9 nm.

90. A method for treating endotoxemia in a patient in need thereof comprising administering a therapeutically effective amount of at least one micelle of claim 15 to the patient.

91. A method for treating at least one symptom of endotoxemia associated with gram negative bacteria in a patient in need thereof comprising administering a therapeutically effective amount of at least one micelle of claim 15 to the patient.

92. The method of claim 91, wherein the at least one symptom is selected from the group consisting of fever, inflammation, disseminated intravascular coagulation, hypotension, renal dysfunction, acute renal failure, acute respiratory distress syndrome, adult respiratory distress syndrome, hepatocellular destruction and cardiac failure.

93. A method for treating septic shock in a patient in need thereof comprising administering a therapeutically effective amount of at least one micelle of claim 15 to the patient.

94. A method for treating systemic inflammatory response syndrome in a patient in need thereof comprising administering a therapeutically effective amount of at least one micelle of claim 15 to the patient.

95. The aqueous solution of claim 19, wherein the micelle has a hydrodynamic diameter of about 7 nm to about 9 nm.

96. A pharmaceutical formulation comprising a therapeutically effective amount of at least one micelle having a hydrodynamic diameter from about 7 nm to about 9 nm, wherein the at least one micelle comprises a compound of formula (IA) or a pharmaceutically acceptable salt thereof; wherein the compound of formula (IA) is:

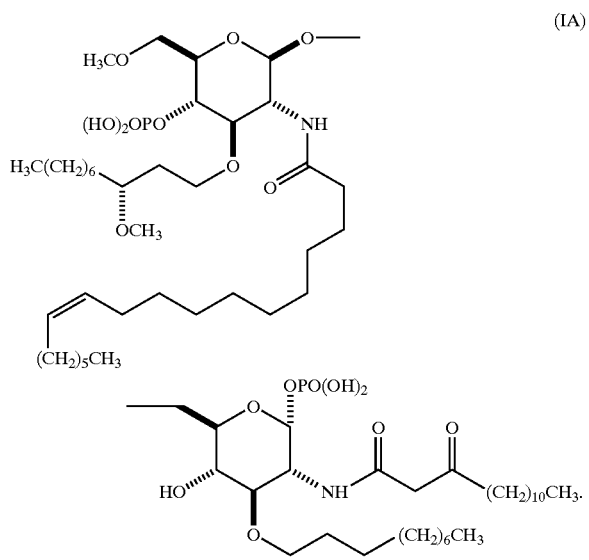

(IA)

* * * * *

UNITED STATES PATENT AND TRADEMARK OFFICE
CERTIFICATE OF CORRECTION

PATENT NO. : 6,906,042 B2
DATED : June 14, 2005
INVENTOR(S) : McShane et al.

It is certified that error appears in the above-identified patent and that said Letters Patent is hereby corrected as shown below:

Title page,
Item [57], ABSTRACT,
Lines 2-4, change each occurrence of "micells," to correctly recite -- micelles, --.
Line 5, change "inflamatory" to correctly recite -- inflammatory --.

Column 21,
Lines 1-17, delete the following:
"
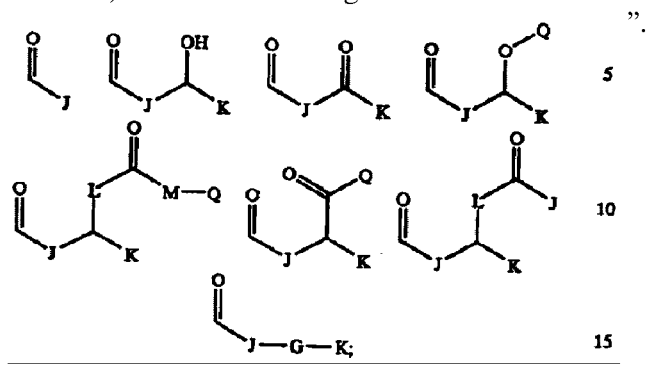
".

Line 21, in the definition of $R^2$, "$C_{1-15}$" should be changed to correctly recite -- $C_{5-15}$ --.
Lines 38-49, delete the following:
"
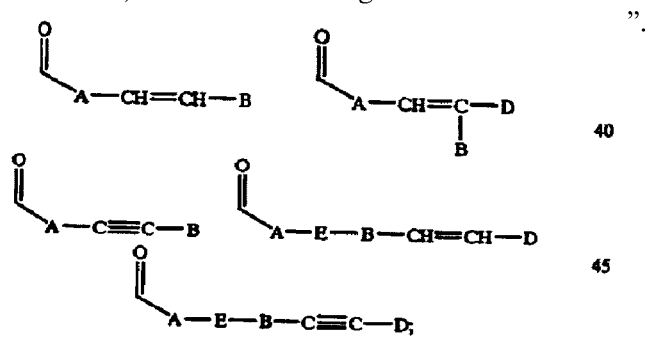
".

Column 22,
Lines 13-20, delete the following:
"
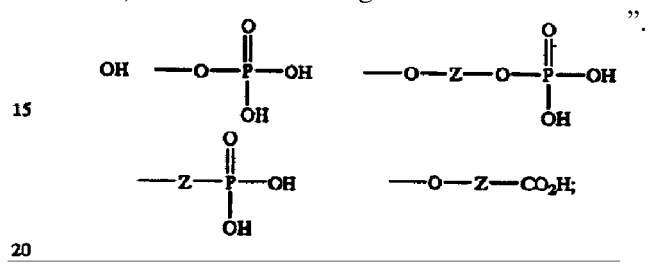
".

UNITED STATES PATENT AND TRADEMARK OFFICE
CERTIFICATE OF CORRECTION

PATENT NO. : 6,906,042 B2
DATED : June 14, 2005
INVENTOR(S) : McShane et al.

It is certified that error appears in the above-identified patent and that said Letters Patent is hereby corrected as shown below:

Column 23,
Lines 50-60, delete the following:
"
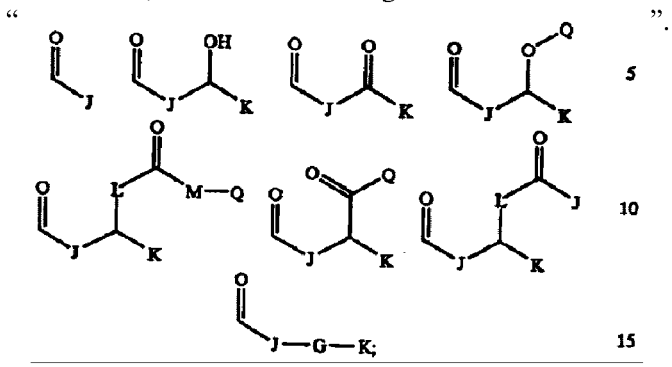
".

Column 24,
Lines 15-25, delete the following:
"
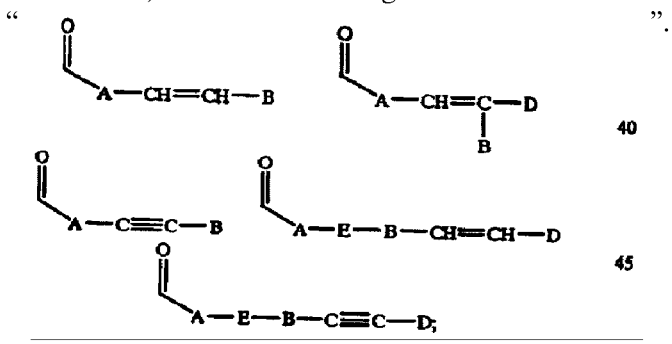
".

Line 29, in the definition of A, B and D, "$C_{4-20}$" should be changed to correctly recite -- $C_{1-15}$ --.
Line 30, in the definition of $R^4$, "$C_{1-15}$" should be changed to correctly recite -- $C_{4-20}$ --.
Lines 55-62, delete the following:
"
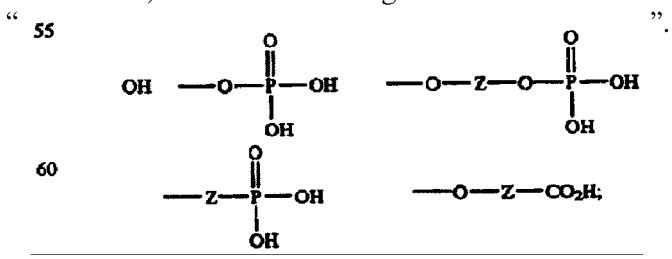
".

UNITED STATES PATENT AND TRADEMARK OFFICE
CERTIFICATE OF CORRECTION

PATENT NO. : 6,906,042 B2  
DATED : June 14, 2005  
INVENTOR(S) : McShane et al.

Page 3 of 6

It is certified that error appears in the above-identified patent and that said Letters Patent is hereby corrected as shown below:

Column 25,  
Lines 30-43, delete the following:
"
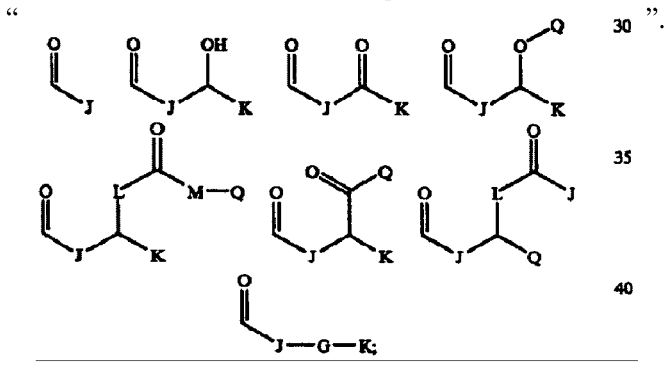
".

Lines 63-66, delete the following:
"
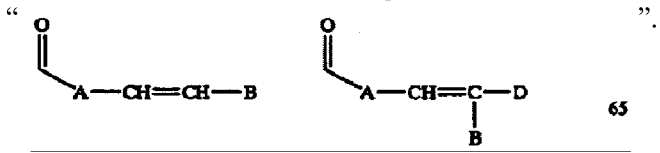
".

Column 26,  
Lines 1-9, delete the following:
"
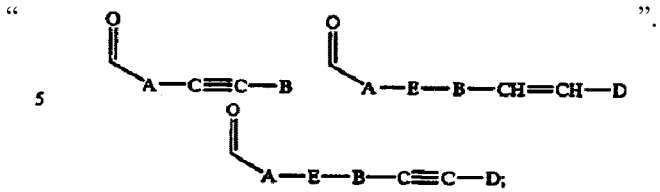
".

Line 19, in the definition of U and V, "$C_{2-5}$" should be changed to correctly recite -- $C_{2-15}$ --.

Lines 38-45, delete the following:
"
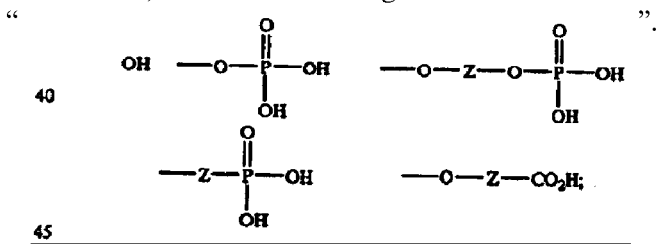
".

Column 27,  
Lines 25-26, change "$CH_2)_2CH(OCH_3)(CH_2)_6CH_3$" to correctly recite -- $(CH_2)_2CH(OCH_3)(CH_2)_6CH_3$ --.

UNITED STATES PATENT AND TRADEMARK OFFICE
CERTIFICATE OF CORRECTION

PATENT NO. : 6,906,042 B2
DATED : June 14, 2005
INVENTOR(S) : McShane et al.

It is certified that error appears in the above-identified patent and that said Letters Patent is hereby corrected as shown below:

Column 28,
Line 3, change "$CH_2)_2CH(OCH_3)(CH_2)_6CH_3$" to correctly recite
-- $(CH_2)_2CH(OCH_3)(CH_2)_6CH_3$ --.

Column 29,
Line 10, change "of claim 44, to" to correctly recite -- of claim 44 to --.

Column 30,
Lines 6-18, delete the following:
"
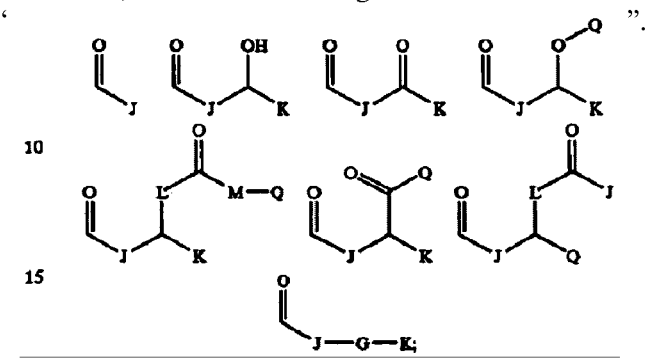
".

Lines 39-49, delete the following:
"
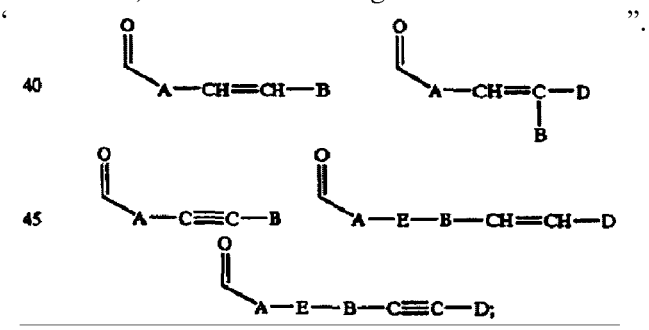
".

Column 31,
Lines 12-20, delete the following:
"
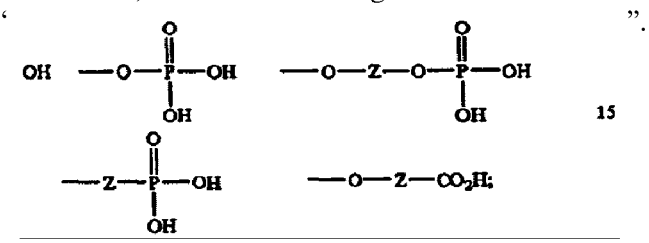
".

UNITED STATES PATENT AND TRADEMARK OFFICE
CERTIFICATE OF CORRECTION

PATENT NO. : 6,906,042 B2
DATED : June 14, 2005
INVENTOR(S) : McShane et al.

It is certified that error appears in the above-identified patent and that said Letters Patent is hereby corrected as shown below:

Column 32,
Line 39, change "$CH_2)_2CH(OCH_3)(CH_2)_6CH_3$" to correctly recite
-- $(CH_2)_2CH(OCH_3)(CH_2)_6CH_3$ --.

Column 34,
Lines 63-66, delete the following:
"

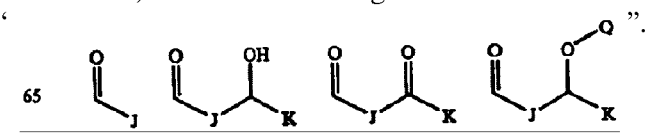

".

Column 35,
Lines 1-11, delete the following:
"

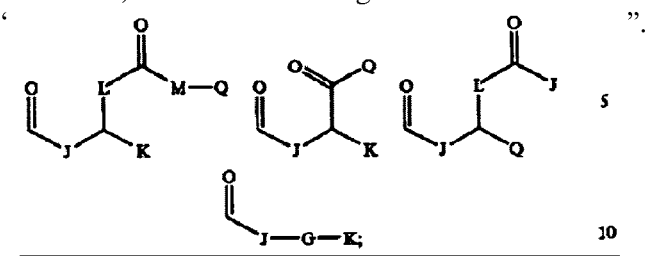

".

Line 14, in the definition of J, K and Q, change "$C_{1-5}$" to correctly recite -- $C_{1-15}$ --.
Lines 30-41, delete the following:
"

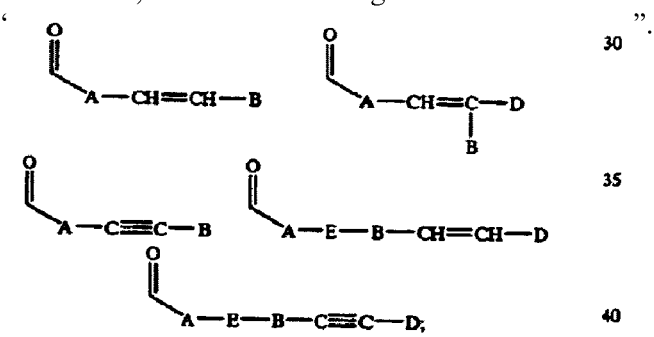

".

Line 44, in the definition of A, B and D, change "$C_{1-5}$" to correctly recite -- $C_{1-15}$ --.

UNITED STATES PATENT AND TRADEMARK OFFICE
CERTIFICATE OF CORRECTION

PATENT NO. : 6,906,042 B2
DATED : June 14, 2005
INVENTOR(S) : McShane et al.

It is certified that error appears in the above-identified patent and that said Letters Patent is hereby corrected as shown below:

Column 36,
Lines 6-14, delete the following:

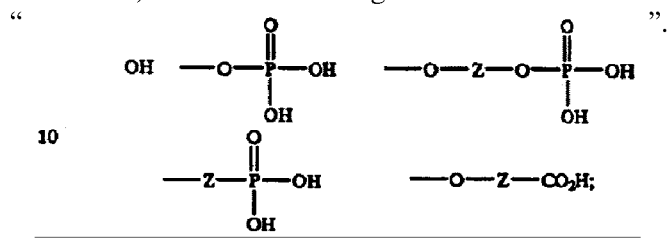

Line 58, change "–CO(CH$_2$)$_9$CH=CH(CH$_2$)$_5$CH$_3$R$^4$" to correctly recite -- –CO(CH$_2$)$_9$CH=CH(CH$_2$)$_5$CH$_3$; and R$^4$ --.
Line 61, change "CH$_2$)$_2$CH(OCH$_3$)(CH$_2$)$_6$CH$_3$" to correctly recite -- (CH$_2$)$_2$CH(OCH$_3$)(CH$_2$)$_6$CH$_3$ --.

Signed and Sealed this

Twenty-fifth Day of October, 2005

JON W. DUDAS
*Director of the United States Patent and Trademark Office*

(12) EX PARTE REEXAMINATION CERTIFICATE (9189th)
United States Patent
McShane et al.

(10) Number: US 6,906,042 C1
(45) Certificate Issued: Aug. 14, 2012

(54) MICELLES

(75) Inventors: James McShane, Wake Forest, NC (US); Tori Arens, Raleigh, NC (US); Kazuhiro Kaneko, Tsukuba (JP); Tomohiro Watanabe, Tsukuba (JP); Kazuhide Ashizawa, Tsukuba (JP)

(73) Assignee: Eisai R&D Management Co., Ltd., Bunkyo, Ku, Tokyo (JP)

Reexamination Request:
No. 90/011,524, Mar. 2, 2011

Reexamination Certificate for:
Patent No.: 6,906,042
Issued: Jun. 14, 2005
Appl. No.: 10/204,227
Filed: Oct. 3, 2002

Certificate of Correction issued Oct. 25, 2005.

(22) PCT Filed: Feb. 20, 2001

(86) PCT No.: PCT/US01/05297
§ 371 (c)(1),
(2), (4) Date: Oct. 3, 2002

(87) PCT Pub. No.: WO01/60382
PCT Pub. Date: Aug. 23, 2001

Related U.S. Application Data
(60) Provisional application No. 60/183,768, filed on Feb. 18, 2000.

(51) Int. Cl.
*A61K 9/107* (2006.01)
*A61K 9/19* (2006.01)
*A61K 31/665* (2006.01)
*A61K 31/70* (2006.01)

(52) U.S. Cl. .......... 514/53; 424/400; 536/17.1; 536/17.2; 536/18.7; 536/55; 536/55.2; 536/55.3

(58) Field of Classification Search .......... 514/53
See application file for complete search history.

(56) References Cited

To view the complete listing of prior art documents cited during the proceeding for Reexamination Control Number 90/011,524, please refer to the USPTO's public Patent Application Information Retrieval (PAIR) system under the Display References tab.

*Primary Examiner* — Bruce Campell

(57) ABSTRACT

The invention provides micelles, pharmaceutical formulations comprising micelles, solutions comprising micelles, methods for preparing micelles, methods for delivering micelles to patients, and methods for treating sepsis, endotoxemia, septic shock and systemic inflammatory response syndrome in patients by adiministering micelles. The micelles comprises compounds of Forumala (A):

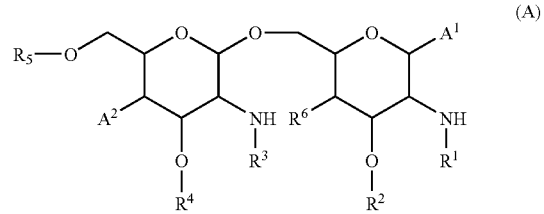

wherein the substituents are as defined herein.

US 6,906,042 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2, 4-8, 39, 87 and 88 is confirmed.

Claims 47-50, 58, 59, 69, 70, 89, 95 and 96 are cancelled.

Claims 3, 9-12, 15-19, 21, 23, 28, 32-38, 40-46, 57, 60, 61, 68, 71, 72, 82-86, 90, 91, 93 and 94 are determined to be patentable as amended.

Claims 13, 14, 20, 22, 24-27, 29-31, 51-56, 62-67, 73-81 and 92, dependent on an amended claim, are determined to be patentable.

New claims 97-111 are added and determined to be patentable.

3. The method of claim 1, wherein Compound (1) is Compound ([1A]*IA*) or a pharmaceutically acceptable salt thereof:

(IA)

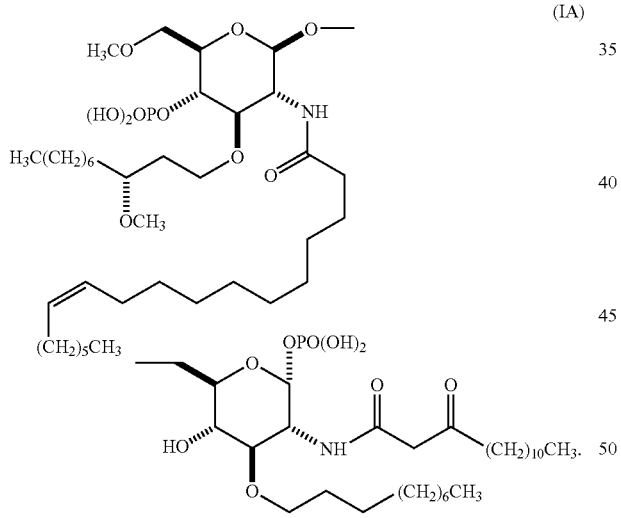

9. [A micelle] *Micelles* produced by the method of claim 1 or claim 2, *wherein the mean hydrodynamic diameter of the micelles is about 6 nm to about 14 nm, and the mean hydrodynamic diameter of the micelles does not substantially change upon freeze-drying and reconstitution.*

10. A method of delivering [a micelle] *micelles* to a patient comprising intravenously administering the [micelle] *micelles* of claim 9 to the patient.

11. A method for treating sepsis in a patient in need thereof comprising intravenously administering an effective amount of the [micelle] *micelles* of claim 9 to the patient.

12. An aqueous solution comprising [at least one micelle] *micelles* prepared by the method of claim 1 or claim 2, *wherein the mean hydrodynamic diameter of the micelles is about 6 nm to about 14 nm, and the mean hydrodynamic diameter of the micelles does not substantially change upon freeze-drying and reconstitution.*

15. [A micelle] *Micelles* comprising Compound (1), a pharmaceutically acceptable salt thereof, and/or a stereoisomer thereof, wherein the [micelle has] *micelles have a mean* hydrodynamic diameter of about [5] *7* nm to about [20] *9* nm, *or about 8 nm to about 10 nm, or about 9 nm to about 11 nm that does not substantially change upon freeze-drying and reconstitution,* wherein Compound (1) is:

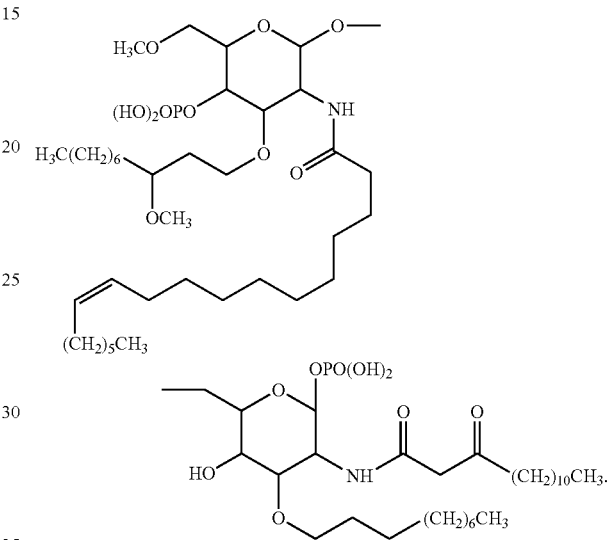

16. The [micelle] *micelles* of claim 15, wherein Compound (1) is Compound (IA) or a pharmaceutically acceptable salt thereof:

(IA)

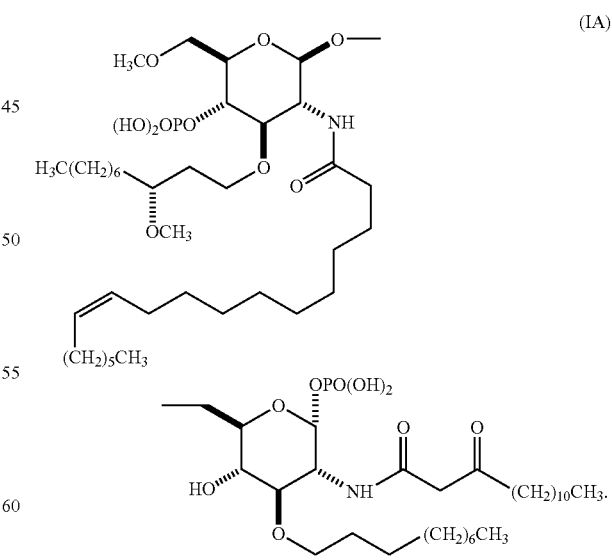

17. A method of delivering [at least one micelle] *micelles* to a patient comprising intravenously administering [at least one micelle] *the micelles* of claim 15 to the patient.

18. A method for treating sepsis in a patient in need thereof comprising intravenously administering an effective amount [at least one micelle] *the micelles* of claim 15 to the patient.

19. An aqueous solution comprising [at least one micelle which comprises] *micelles comprising* Compound (1), a pharmaceutically acceptable salt thereof, and/or a stereoisomer thereof, wherein the [micelle has] *micelles have* a mean hydrodynamic diameter of about [5] *7* nm to about [20] *9* nm, *or about 8 nm to about 10 nm, or about 9 nm to about 11 nm that does not substantially change upon freeze-drying and reconstitution*; and wherein Compound (1) is:

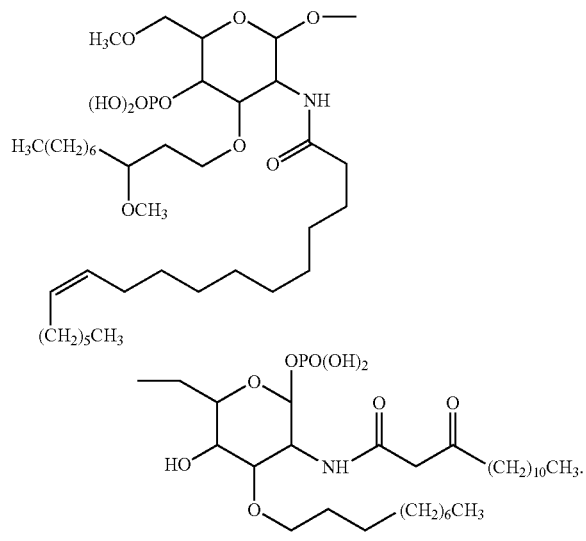

21. A method for delivering [at least one micelle] *micelles* to a patient comprising intravenously administering the aqueous solution of claim 19 to the patient.

23. A method for preparing at least one micelle comprising a compound of Formula (A), a pharmaceutically acceptable salt thereof, and/or a stereoisomer thereof; wherein the method comprises:

adding an amount of [Compound] *the compound of Formula* (A), a pharmaceutically acceptable salt thereof, and/or a stereoisomer thereof to a first aqueous alkaline solution comprising at least one basic metal salt, at least one neutral metal salt, and a predetermined concentration of metal ion; thereby forming a second aqueous alkaline solution comprising at least one micelle with a preselected hydrodynamic diameter, wherein the at least one micelle comprises [a] *the* compound of Formula (A), a pharmaceutically acceptable salt thereof, and/or a stereoisomer thereof; wherein the compound of [formula] *Formula* (A) is:

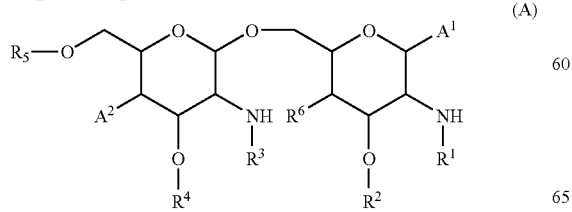

(A)

wherein $R^1$ is selected from the group consisting of:

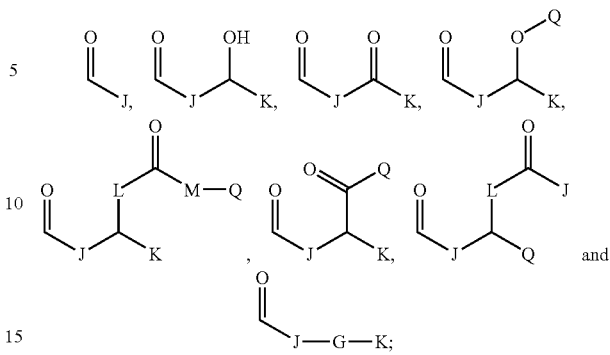

J, K and Q are each independently a straight or branched $C_{1-15}$ alkyl; L is O, N or C; M is O Or N; G is N, O, S, SO or $SO_2$; $R^2$ is a straight or branched $C_{5-15}$ alkyl;

$R^3$ *is* selected from the group consisting of:

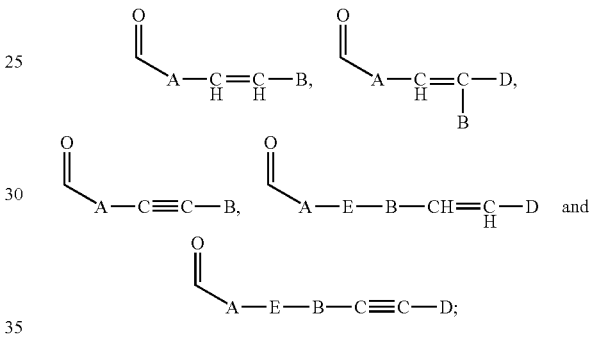

E is N, O, S, SO or $SO_2$; A, B and D are each independently a straight or branched $C_{1-15}$ alkyl group;

$R^4$ is a straight or branched $C_{4-20}$ alkyl group or

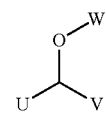

U and V are each independently a straight or branched $C_{2-15}$ alkyl group; W is a hydrogen or a straight or branched $C_{1-5}$ alkyl group; $R^5$ is hydrogen, —J', —J'—OH, —J'—O—K', —J'—O—K'—OH or J'—O—PO$(OH)_2$; J' and K' are each independently a straight or branched $C_{1-5}$ alkyl group; $R^6$ is hydroxy, halogen, a $C_{1-5}$ alkoxy group or a $C_{1-5}$ acyloxy group; $A^1$ and $A^2$ are each independently selected from the group consisting of:

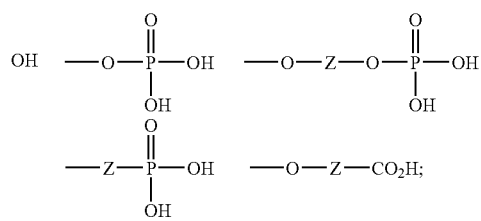

Z is a straight or branched $C_{1-10}$ alkyl group.

28. The method of claim 23, further comprising:

adding the second aqueous alkaline solution to a third aqueous solution comprising a buffer system or at least one strong acid; thereby forming a fourth aqueous solution having a neutral pH relative to the pH of the second aqueous alkaline solution, wherein the fourth aqueous solution comprises at least one micelle having a preselected hydrodynamic diameter that is substantially the same as the preselected hydrodynamic diameter of the at least one micelle in the second aqueous alkaline solution;

wherein the at least one micelle in the fourth aqueous solution and the at least one micelle in the second aqueous solution comprise [a] *the* compound of Formula (A), a pharmaceutically acceptable salt thereof, and/or a stereoisomer thereof.

32. [A micelle] *Micelles* produced by the method of claim 23 or claim 28, *wherein the mean hydrodynamic diameter of the micelles is about 6 nm to about 14 nm, and the mean hydrodynamic diameter of the micelles does not substantially change upon freeze-drying and reconstitution.*

33. A method of delivering [at least one micelle] *micelles* to a patient comprising intravenously administering [at least one micelle] *micelles* of claim 32 to the patient.

34. An aqueous solution comprising [at least one micelle] *micelles* produced by the method of claim 23 or claim 28, *wherein the mean hydrodynamic diameter of the micelles is about 6 nm to about 14 nm, and the mean hydrodynamic diameter of the micelles does not substantially change upon freeze-drying and reconstitution.*

35. A method of delivering [at least one micelle] *micelles* to a patient comprising intravenously administering the aqueous solution of claim 34 to the patient.

36. The method of claim 3, wherein both hydrogen atoms in both —OPO(OH)$_2$ groups in [the compound of formula] *Compound* (IA) are replaced with sodium.

37. The micelle of claim 16, wherein both hydrogen atoms in both —OPO(OH)$_2$ groups in [the compound of formula] *Compound* (IA) are replaced with sodium.

38. The aqueous solution of claim 20, wherein both hydrogen atoms in both —OPO(OH)$_2$ groups in [the compound of formula] *Compound* (IA) are replaced with sodium.

40. [A micelle] *Micelles* comprising [Compound] *a compound of Formula* (A), a pharmaceutically acceptable salt thereof, and/or a stereoisomer thereof, wherein the [micelle has] *micelles have a mean* hydrodynamic diameter of about [5] *6* nm to about [100] *14* nm *that does not substantially change upon freeze-drying and reconstitution*; wherein [Compound] *the compound of Formula* (A) is:

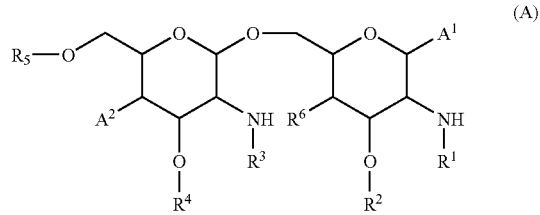

(A)

wherein R$^1$ is selected from the group consisting of:

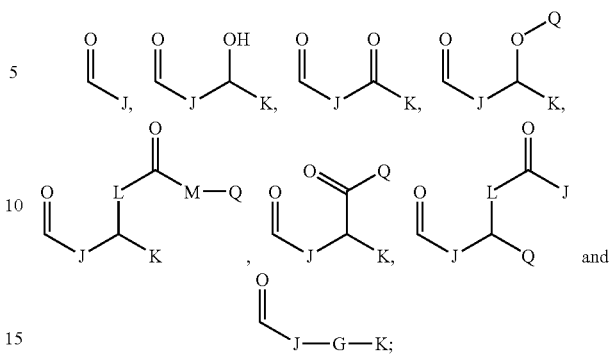

and

J, K and Q are each independently a straight or branched C$_{1-15}$ alkyl; L is O, N or C; M is O or N; G is N, O, S, SO or SO$_2$; R$^2$ is a straight or branched C$_{5-15}$ alkyl;

R$^3$ is selected from the group consisting of:

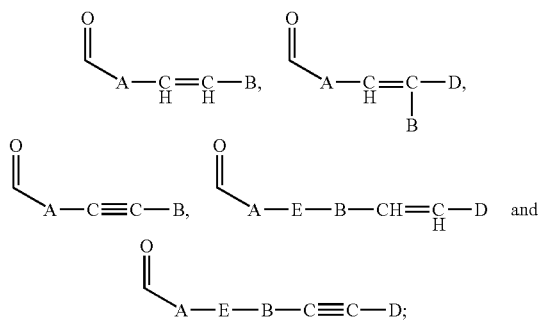

and

E is N, O, S, SO or SO$_2$; A, B and D are each independently a straight or branched C$_{1-15}$ alkyl group; R$^4$ is a straight or branched C$_{4-20}$ alkyl group or

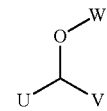

U and V are each independently a straight or branched C$_{2-15}$ alkyl group; W is a hydrogen or a straight or branched C$_{1-5}$ alkyl group; R$^5$ is hydrogen, —J', —J'—OH, —J'—O—K', —J'—O—K'—OH or J'—O—PO(OH)$_2$: J' and K' are each independently a straight or branched C$_{1-5}$ alkyl group; R$^6$ is hydroxy, halogen, a C$_{1-5}$ alkoxy group or a C$_{1-5}$ acyloxy group; A$^1$ and A$^2$ are each independently selected from the group consisting of:

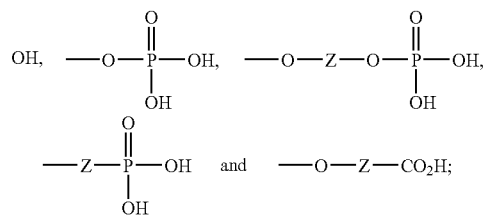

Z is a straight or branched C$_{1-10}$ alkyl group.

41. An aqueous solution comprising [at least one micelle which comprises Compound] *micelles comprising a com-*

*pound of Formula* (A), a pharmaceutically acceptable salt thereof, and/or a stereoisomer thereof, wherein the [at least one micelle has] *micelles have* a *mean* hydrodynamic diameter of about [5] *6* nm to about [100] *14* nm *that does not substantially change upon freeze-drying and reconstitution*; wherein [Compound] *the compound of Formula* (A) is:

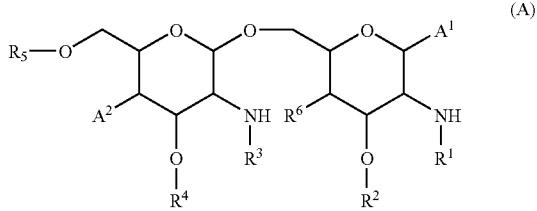

wherein $R^1$ is selected from the group consisting of:

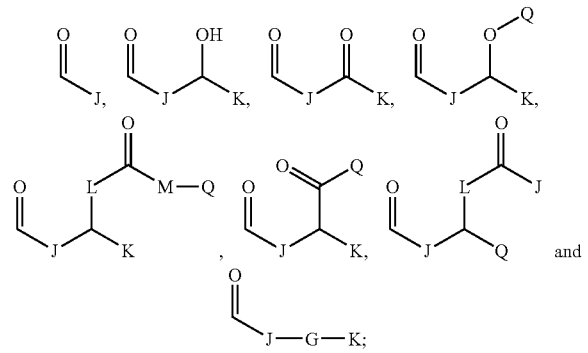

J, K and Q are each independently a straight or branched $C_{1-15}$ alkyl; L is O, N or C; M is O or N; G is N, O, S, SO or $SO_2$; $R^2$ is a straight or branched $C_{5-15}$ alkyl; $R^3$ is selected from the group consisting of:

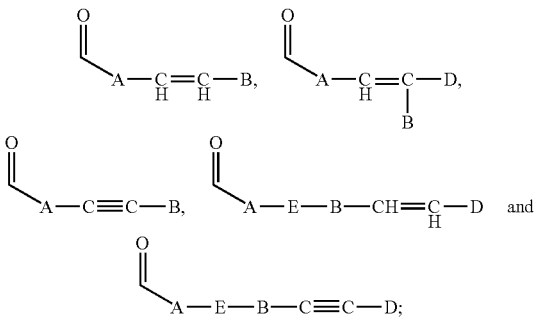

E is N, O, S, SO or $SO_2$; A, B and D are each independently a straight or branched $C_{1-15}$ alkyl group; $R^4$ is a straight or branched $C_{4-20}$ alkyl group or

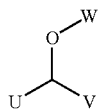

U and V are each independently a straight or branched $C_{2-15}$ alkyl group; W is a hydrogen or a straight or branched $C_{1-5}$ alkyl group; $R^5$ is hydrogen, —J', —J'— OH, —J'—O—K', —J'—O—K'—OH or J'—O—PO $(OH)_2$; J' and K' are each independently a straight or branched $C_{1-5}$ alkyl group; $R^6$ is hydroxyl, halogen, a $C_{1-5}$ alkoxy group or a $C_{1-5}$ acyloxy group; $A^1$ and $A^2$ are each independently selected from the group consisting of:

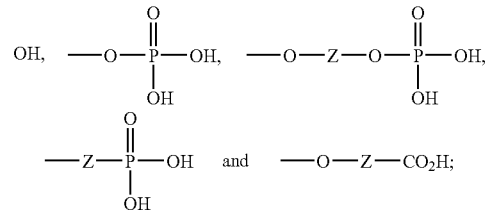

Z is a straight or branched $C_{1-10}$ alkyl group.

42. [A micelle] *Micelles* comprising [Compound] *a compound of Formula* (B), a pharmaceutically acceptable salt thereof, and/or a stereoisomer thereof, wherein the [micelle has] *micelles have* a *mean* hydrodynamic diameter of about [5] *6* nm to about [100] *14* nm *that does not substantially change upon freeze-drying and reconstitution*; wherein [Compound] *the compound of Formula* (B) is:

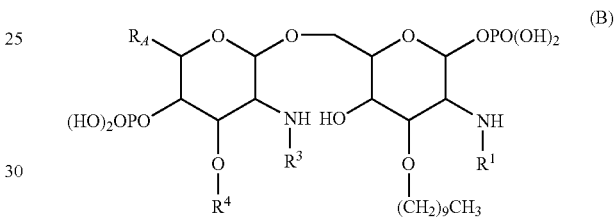

wherein $R_A$ is —$CH_2OCH_3$; $R^1$ is —$COCH_2CO$ $(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$;
wherein $R_A$ is —$CH_2OCH_3$; $R^1$ is —$COCH_2CO$ $(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$COCH_2CO$ $(CH_2)_{10}CH_3$; $R^3$ is —$CO(CH_2)_{16}CH_3$; and $R^4$ is —$(CH_2)_2CH(OH)(CH_2)_6CH_3$;
wherein $R_A$ is —$CH_2OCH_3$; $R^1$ is —$COCH_2CHOH$ $(CH_2)_{10}CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$COCH_2CO$ $(CH_2)_{10}CH_3$; $R^3$ is —$CO(CH_2)_9CH=CH(CH_2)_5CH_3$; and $R^4$ is —$(CH_2)_9CH_3$;
wherein $R_A$ is —$CH_2OCH_3$; $R^1$ is —$CO(CH_2)_9CH=CH$ $(CH_2)_5CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$CO(CH_2)_{12}CH_3$; $R^3$ is —$CO(CH_2)_9CH=CH(CH_2)_5CH_3$; and $R^4$ is —$(CH_2)_2CH(OH)(CH_2)_6CH_3$;
wherein $R_A$ is —$CH_2OCH_3$; $R^1$ is —$COCH_2CH(OCH_3)$ $(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$;
wherein $R_A$ is —$CH_2OCH_3$; $R^1$ is —$COCH_2CH(OCH_3)$ $(CH_2)_{10}CH_3$; $R^3$ is —$CO(CH_2)_9CH=CH(CH_2)_5(CH_3)$; and $R^4$ is —$(CH_2)_2CH(OH)(CH_2)_6CH_3$;
wherein $R_A$ is —$CH_2OCH_3$; $R^1$ is —$COCH_2CH(OH)$ $(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$; or
wherein $R_A$ is —$CH_3$; $R^1$ is —$COCH_2CO(CH_2)_{10}CH_3$; $R^3$ is —$CO(CH_2)_9CH=CH(CH_2)_5CH_3$; and $R^4$ is —$(CH_2)_2CH(OCH_3)(CH_2)_6CH_3$.

43. An aqueous solution comprising [at least one micelle which comprises Compound] *micelles comprising a compound of Formula* (B), a pharmaceutically acceptable salt thereof, and/or a stereoisomer thereof, wherein the [at least one micelle has] *micelles have* a *mean* hydrodynamic diameter of about [5] *6* nm to about [100] *14* nm *that does not substantially change upon freeze-drying and reconstitution*; wherein [Compound] *the compound of Formula* (B) is:

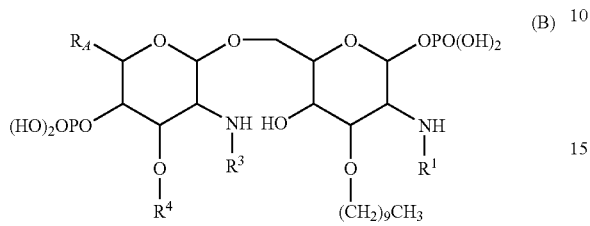

(B)

wherein $R_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$:

wherein $R_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein $R_A$ is —CH$_2$OCH$_3$; R$^1$ is —COCH$_2$CO(CH$_2$)$_{10}$CH$_3$; R$^3$ is —CO(CH$_2$)$_{16}$CH$_3$; and R$^4$ is —(CH$_2$)$_2$CH(OH)(CH$_2$)$_6$CH$_3$;

wherein $R_A$ is —CH$_2$OCH$_3$; R$^1$ is —COCH$_2$CHOH(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein $R_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_9$CH$_3$;

wherein $R_A$ is —CH$_2$OCH$_3$; R$^1$ is —CO(CH$_2$)$_9$CH=CH(CH$_2$)$_5$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein $R_A$ is —CH$_2$OCH$_3$; R$^1$ is —CO(CH$_2$)$_{12}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein $R_A$ is —CH$_2$OCH$_3$; R$^1$ is —COCH$_2$CH(OCH$_3$)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$;

wherein $R_A$ is —CH$_2$OCH$_3$; R$^1$ is —COCH$_2$CH(OCH$_3$)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein $R_A$ is —CH$_2$OCH$_3$; R$^1$ is —COCH$_2$CH(OH)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$; or wherein $R_A$ is —CH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$.

44. A pharmaceutical formulation comprising a therapeutically effective amount of [at least one micelle] *micelles* having a *mean* hydrodynamic diameter from about [1] *7* nm to about [100] *9* nm, *or about 8 nm to about 10 nm, or about 9 nm to about 11 nm that does not substantially change upon freeze-drying and reconstitution,* wherein the [at least one micelle comprises a compound of formula (I)] *micelles comprise Compound (1)*, a pharmaceutically acceptable salt thereof, and/or a stereoisomer thereof; wherein [the compound of formula (I)] *Compound (1)* is:

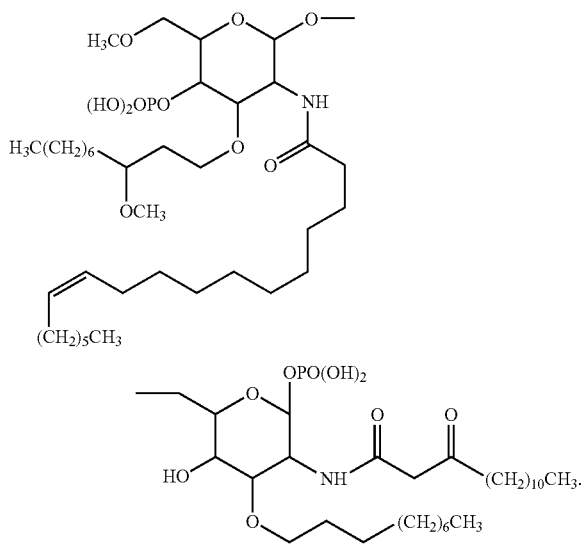

45. The pharmaceutical formulation of claim 44, wherein [the compound of formula (I)] *Compound (1)* is [a compound of formula] *Compound* (IA) or a pharmaceutically acceptable salt thereof; wherein [the compound of formula] *Compound* (IA) is:

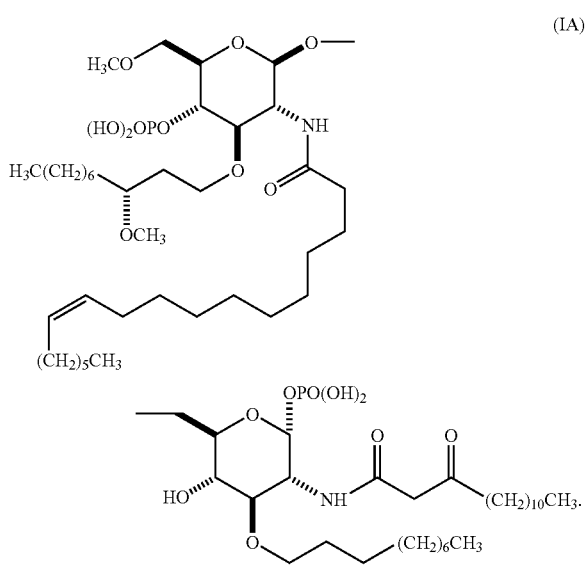

(IA)

46. The pharmaceutical formulation of claim 45, wherein both hydrogen atoms in both —OPO(OH)$_2$ groups in [the compound of formula] *Compound* (IA) are replaced with sodium.

57. A pharmaceutical formulation comprising a therapeutically effective amount of [at least one micelle,] *micelles* having a *mean* hydrodynamic diameter from about [1] *6* nm to about [100] *14* nm *that does not substantially change upon freeze-drying and reconstitution*, wherein the [at least one micelle comprises] *micelles comprise* a compound of [formula] *Formula* (A), a pharmaceutically acceptable salt thereof, and/or a stereoisomer thereof; wherein the compound of [formula] *Formula* (A) is:

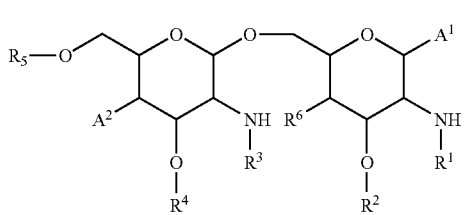

(A)

wherein R¹ is selected from the group consisting of:

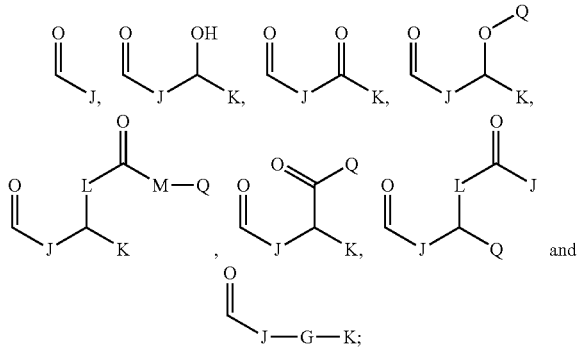

J, K and Q are each independently a straight or branched $C_{1-15}$ alkyl; L is O, N or C; M is O or N; G is N, O, S, SO or $SO_2$; $R^2$ is a straight or branched $C_{5-15}$ alkyl;

$R^3$ is selected from the group consisting of:

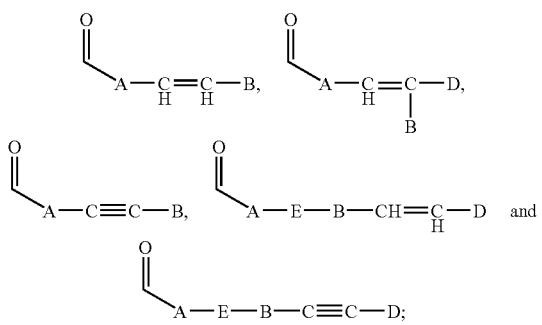

E is N, O, S, SO or $SO_2$; A, B and D are each independently a straight or branched $C_{1-15}$ alkyl group; $R^4$ is a straight or branched $C_{4-20}$ alkyl group or

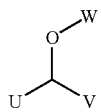

U and V are each independently a straight or branched $C_{2-15}$ alkyl group; W is a hydrogen or a straight or branched $C_{1-5}$ alkyl group; $R^5$ is hydrogen, —J', —J'—OH, —J'—O—K', —J'—O—K'—OH or J'—O—PO$(OH)_2$; J' and K' are each independently a straight or branched $C_{1-5}$ alkyl group; $R^6$ is hydroxy, halogen, a $C_{1-5}$ alkoxy group or a $C_{1-5}$ acyloxy group; $A^1$ and $A^2$ are each independently selected from the group consisting of:

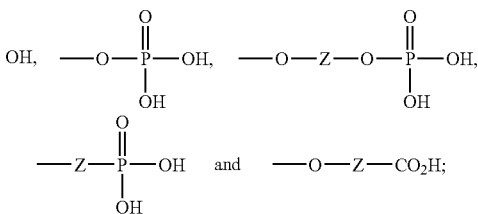

Z is a straight or branched $C_{1-10}$ alkyl group.

60. The pharmaceutical formulation of claim 57, wherein the [at least one micelle has] *micelles have a mean* hydrodynamic diameter from about 7 nm to about [15] *14* nm.

61. The pharmaceutical formulation of claim 57, wherein the [at least one micelle has] *micelles have a mean* hydrodynamic diameter from about 7 nm to about 9 nm.

68. A pharmaceutical formulation comprising a therapeutically effective amount of [at least one micelle,] *micelles* having a *mean* hydrodynamic diameter from about [1] *6* nm to about [100] *14* nm *that does not substantially change upon freeze-drying and reconstitution*, wherein the [at least one micelle comprises] *micelles comprise* a compound of [formula] *Formula* (B), a pharmaceutically acceptable salt thereof, and/or a stereoisomer thereof; wherein the compound of [formula] *Formula* (B) is:

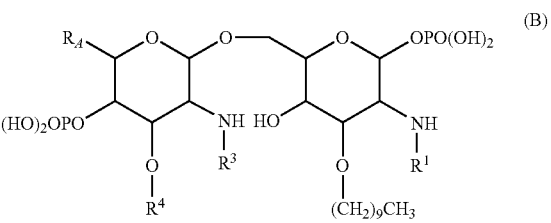

(B)

wherein $R_A$ is —$CH_2OCH_3$; $R^1$ is —$COCH_2CO$ $(CH_2)_{10}CH_3$; $R^3$ is —$CO(CH_2)_9CH$=$CH(CH_2)_5CH_3$; and $R^4$ is —$(CH_2)_2CH(OCH_3)(CH_2)_6CH_3$;

wherein $R_A$ is —$CH_2OCH_3$; $R^1$ is —$COCH_2CO$ $(CH_2)_{10}CH_3$; $R^3$ is —$CO(CH_2)_9CH$=$CH(CH_2)_5CH_3$; and $R^4$ is —$(CH_2)_2CH(OH)(CH_2)_6CH_3$;

wherein $R_A$ is —$CH_2OCH_3$; $R^1$ is —$COCH_2CO$ $(CH_2)_{10}CH_3$; $R^3$ is —$CO(CH_2)_{16}CH_3$; and $R^4$ is —$(CH_2)_2CH(OH)(CH_2)_6CH_3$;

wherein $R_A$ is —$CH_2OCH_3$; $R^1$ is —$COCH_2CHOH$ $(CH_2)_{10}CH_3$; $R^3$ is —$CO(CH_2)_9CH$=$CH(CH_2)_5CH_3$; and $R^4$ is —$(CH_2)_2CH(OH)(CH_2)_6CH_3$;

wherein $R_A$ is —$CH_2OCH_3$; $R^1$ is —$COCH_2CO$ $(CH_2)_{10}CH_3$; $R^3$ is —$CO(CH_2)_9CH$=$CH(CH_2)_5CH_3$; and $R^4$ is —$(CH_2)_9CH_3$;

wherein $R_A$ is —$CH_2OCH_3$; $R^1$ is —$CO(CH_2)_9CH$=$CH$ $(CH_2)_5CH_3$; $R^3$ is —$CO(CH_2)_9CH$=$CH(CH_2)_5CH_3$; and $R^4$ is —$(CH_2)_2CH(OH)(CH_2)_6CH_3$;

wherein $R_A$ is —$CH_2OCH_3$; $R^1$ is —$CO(CH_2)_{12}CH_3$; $R^3$ is —$CO(CH_2)_9CH$=$CH(CH_2)_5CH_3$; and $R^4$ is —$(CH_2)_2CH(OH)(CH_2)_6CH_3$;

where $R_A$ is —$CH_2OCH_3$; $R^1$ is —$COCH_2CH(OCH_3)$ $(CH_2)_{10}CH_3$; $R^3$ is —$CO(CH_2)_9CH$=$CH(CH_2)_5CH_3$; and $R^4$ is —$(CH_2)_2CH(OCH_3)(CH_2)_6CH_3$;

wherein $R_A$ is —$CH_2OCH_3$; $R^1$ is —$COCH_2CH(OCH_3)$ $(CH_2)_{10}CH_3$; $R^3$ is —$CO(CH_2)_9CH$=$CH(CH_2)_5CH_3$; and $R^4$ is —$(CH_2)_2CH(OH)(CH_2)_6CH_3$;

wherein $R_A$ is —$CH_2OCH_3$; $R^1$ is —$COCH_2CH(OH)$ $(CH_2)_{10}CH_3$; $R^3$ is —$CO(CH_2)_9CH$=$CH(CH_2)_5CH_3$; and $R^4$ is —$(CH_2)_2CH(OCH_3)(CH_2)_6CH_3$; or wherein R₄ is —CH₃; R¹ is —COCH₂CO(CH₂)₁₀CH₃; R³ is —CO(CH₂)₉CH═CH(CH₂)₅CH₃; and R⁴ is —(CH₂)₂CH(OCH₃)(CH₂)₆CH₃.

71. The pharmaceutical formulation of claim 68, wherein the [at least one micelle has] *micelles have* a *mean* hydrodynamic diameter from about 7 nm to about [15] *14* nm.

72. The pharmaceutical formulation of claim 68, wherein the [at least one micelle has] *micelles have* a *mean* hydrodynamic diameter from about 7 nm to about 9 nm.

82. A lyophilized drug product comprising a therapeutically effective amount of [at least one micelle,] *micelles* having a *mean* hydrodynamic diameter from about [5] *7* nm to about [100] *9 nm, or about 8 nm to about 10 nm, or about 9 nm to about 11 nm prior to lyophilization that does not substantially change upon reconstitution,* wherein the [at least one micelle comprises a compound of formula (I)] *micelles comprise Compound (1)*, a pharmaceutically acceptable salt thereof, and/or a stereoisomer thereof; wherein [the compound of formula (I)] *Compound (1)* is:

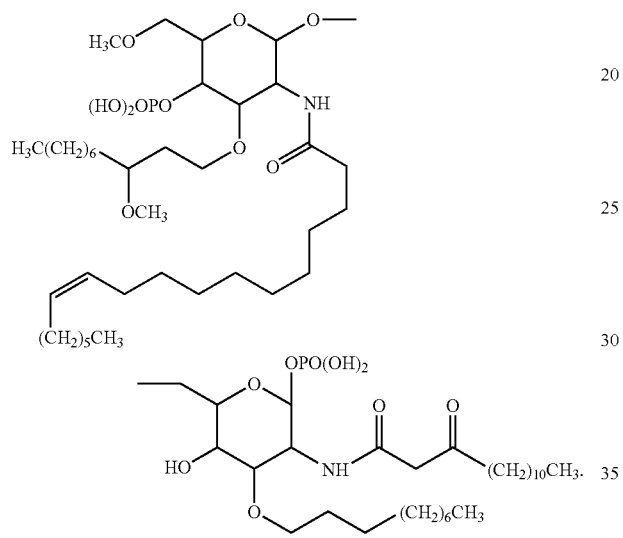

83. The lyophilized drug product of claim 82, wherein [the compound of formula (I)] *Compound (1)* is [a compound of formula] *Compound* (IA) or a pharmaceutically acceptable salt thereof; wherein [the compound of formula] *Compound* (IA) is:

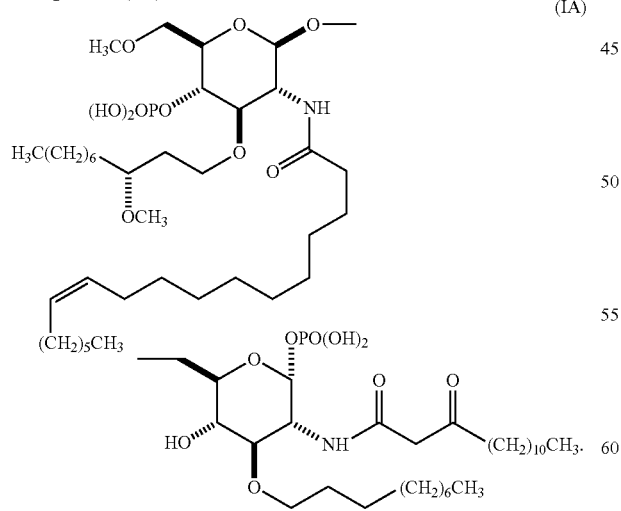

84. The lyophilized drug product of claim 83, wherein both hydrogen atoms in both —OPO(OH)₂ groups in [the compound of formula] *Compound* (IA) are replaced with sodium.

85. A lyophilized drug product comprising a therapeutically effective amount of [at least one micelle,] *micelles* having a *mean* hydrodynamic diameter from about [5] *6* nm to about [100] *14* nm *prior to lyophilization that does not substantially change upon reconstitution*, wherein the [at least one micelle comprises] *micelles comprise* a compound of [formula] *Formula* (A), a pharmaceutically acceptable salt thereof, and/or a stereoisomer thereof; wherein the compound of [formula] *Formula* (A) is:

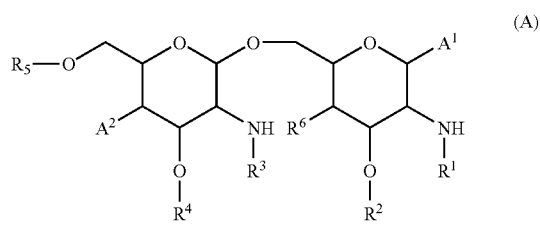

wherein R¹ is selected from the group consisting of:

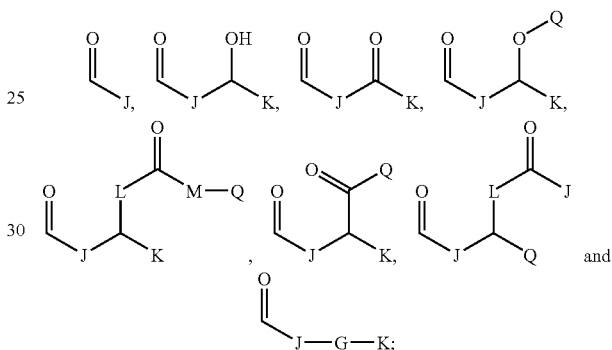

J, K and Q are each independently a straight or branched C₁₋₁₅ alkyl; L is O, N or C; M is O or N; G is N, O, S, SO or SO₂; R² is a straight or branched C₅₋₁₅ alkyl;

R³ is selected from the group consisting of:

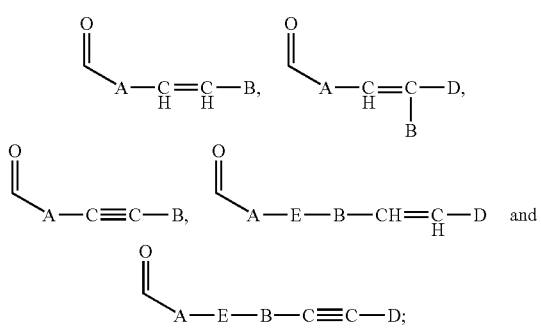

E is N, O, S, SO or SO₂; A, B and D are each independently a straight or branched C₁₋₁₅ alkyl group; R⁴ is a straight or branched C₄₋₂₀ alkyl group or

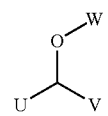

U and V are each independently a straight or branched C₂₋₁₅ alkyl group; W is a hydrogen or a straight or branched C₁₋₅ alkyl group; R⁵ is hydrogen, —J', —J'—

OH, —J'—O—K', —J'—O—K'—OH or J'—O—PO(OH)$_2$; J' and K' are each independently a straight or branched C$_{1-5}$ alkyl group; R$^6$ is hydroxy, halogen, a C$_{1-5}$ alkoxy group or a C$_{1-5}$ acyloxy group; A$^1$ and A$^2$ are each independently selected from the group consisting of:

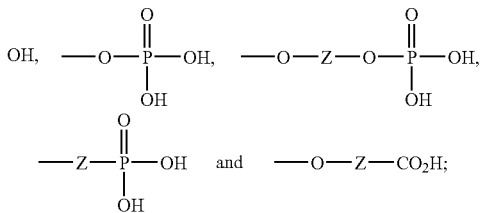

Z is a straight or branched C$_{1-10}$ alkyl group.

86. A lyophilized drug product comprising a therapeutically effective amount of [at least one micelle,] *micelles* having a *mean* hydrodynamic diameter *upon freeze-drying* from about [5] *6* nm to about [100] *20* nm *prior to lyophilization that does not substantially change upon reconstitution*, wherein the [at least one micelle comprises] *micelles comprise* a compound of [formula] *Formula* (B), a pharmaceutically acceptable salt thereof, and/or a stereoisomer thereof; wherein the compound of [formula] *Formula* (B) is:

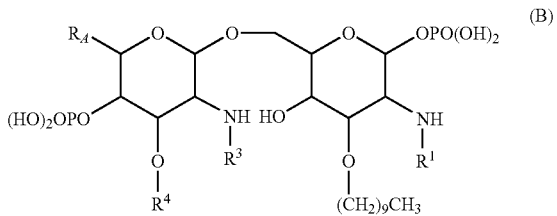

wherein R$_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$;

wherein R$_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein R$_A$ is —CH$_2$OCH$_3$; R$^1$ is —COCH$_2$CO(CH$_2$)$_{10}$CH$_3$; R$^3$ is —CO(CH$_2$)$_{16}$CH$_3$; and R$^4$ is —(CH$_2$)$_2$CH(OH)(CH$_2$)$_6$CH$_3$;

wherein R$_A$ is —CH$_2$OCH$_3$; R$^1$ is —COCH$_2$CHOH(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein R$_A$ is —CH$_2$OCH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_6$CH$_3$;

wherein R$_A$ is —CH$_2$OCH$_3$; R$^1$ is —CO(CH$_2$)$_9$CH=CH(CH$_2$)$_5$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein R$_A$ is —CH$_2$OCH$_3$; R$^1$ is —CO(CH$_2$)$_{12}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein R$_A$ is —CH$_2$OCH$_3$; R$^1$ is —COCH$_2$CH(OCH$_3$)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$;

wherein R$_A$ is —CH$_2$OCH$_3$; R$^1$ is —COCH$_2$CH(OCH$_3$)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OH)(CH$_2$)$_6$CH$_3$;

wherein R$_A$ is —CH$_2$OCH$_3$; R$^1$ is —COCH$_2$CH(OH)(CH$_2$)$_{10}$CH$_3$; R$^3$ is —CO(CH$_2$)$_9$CH=CH(CH$_2$)$_5$CH$_3$; and R$^4$ is —(CH$_2$)$_2$CH(OCH$_3$)(CH$_2$)$_6$CH$_3$; or wherein R$_A$ is —CH$_3$; R$^1$ is —COCH$_2$CO(CH$_2$)$_{10}$CH$_3$; R$^3$ is —CO(CH$_2$)$_9$CH=CH(CH$_2$)$_5$CH$_3$; and R$^4$ is —(CH$_2$)$_2$ CH(OCH$_3$)(CH$_2$)$_6$CH$_3$.

90. A method for treating endotoxemia in a patient in need thereof comprising administering a therapeutically effective amount of [at least one micelle] *micelles* of claim 15 to the patient.

91. A method for treating at least one symptom of endotoxemia associated with gram negative bacteria in a patient in need thereof comprising administering a therapeutically effective amount of [at least one micelle] *micelles* claim 15 to the patient.

93. A method for treating septic shock in a patient in need thereof comprising administering a therapeutically effective amount of [at least one micelle] *micelles* of claim 15 to the patient.

94. A method for treating systemic inflammatory response syndrome in a patient in need thereof comprising administering a therapeutically effective amount of [at least one micelle] *micelles* of claim 15 to the patient.

97. *The micelles of claim 15, 40, or 42, wherein the mean hydrodynamic diameter does not substantially change by more than 0.5 nm, 1 nm, or 2 nm.*

98. *The aqueous solution of claim 19, 41, or 43, wherein the mean hydrodynamic diameter does not substantially change by more than 0.5 nm, 1 nm, or 2 nm.*

99. *The pharmaceutical formulation of claim 44, 57, or 68, wherein the mean hydrodynamic diameter does not substantially change by more than 0.5 nm, 1 nm, or 2 nm.*

100. *The lyophilized drug product of claim 82, 85, or 86, wherein the mean hydrodynamic diameter does not substantially change by more than 0.5 nm, 1 nm, or 2 nm.*

101. *The micelles of claim 15, 40, or 42, wherein the mean hydrodynamic diameter is preselected.*

102. *The aqueous solution of claim 19, 41, or 43, wherein the mean hydrodynamic diameter is preselected.*

103. *The pharmaceutical formulation of claim 44, 57, or 68, wherein the mean hydrodynamic diameter is preselected.*

104. *The lyophilized drug product of claim 82, 85, or 86, wherein the mean hydrodynamic diameter is preselected.*

105. *The micelles of claim 15, 40, or 42, wherein the mean hydrodynamic diameter of the micelles does not substantially change upon reconstitution after storage in a freeze-dried form for six months at from about 2° to about 25° C.*

106. *The aqueous solution of claim 19, 41, or 43, wherein the mean hydrodynamic diameter of the micelles does not substantially change upon reconstitution after storage in a freeze-dried form for six months at from about 2° to about 25° C.*

107. *The pharmaceutical formulation of claim 44, 57, or 68, wherein the mean hydrodynamic diameter of the micelles does not substantially change upon reconstitution after storage in a freeze-dried form for six months at from about 2° to about 25° C.*

108. *The lyophilized drug product of claim 82, 85, or 86, wherein the mean hydrodynamic diameter of the micelles does not substantially change upon reconstitution after storage in a freeze-dried form for six months at from about 2° to about 25° C.*

109. *The micelles of claim 40 or 42, having a mean hydrodynamic diameter from about 7 nm to about 9 nm.*

110. *The aqueous solution of claim 41 or 43, wherein the micelles have a mean hydrodynamic diameter from about 7 nm to about 9 nm.*

111. *The lyophilized drug product of claim 85 or 86, wherein the micelles have a mean hydrodynamic diameter from about 7 nm to about 9 nm.*

\* \* \* \* \*